US011957606B2

(12) United States Patent
Dechev et al.

(10) Patent No.: US 11,957,606 B2
(45) Date of Patent: Apr. 16, 2024

(54) LOW-COST PROSTHETIC APPARATUS, METHODS, KITS, AND SYSTEMS WITH IMPROVED FORCE TRANSFER ELEMENTS

(71) Applicant: Victoria Hand Project, Victoria (CA)

(72) Inventors: Nikolai Dechev, Victoria (CA); Michael Carl Veikko Peirone, Victoria (CA); Kelly Knights, Victoria (CA); Kimberly Arklie, Victoria (CA)

(73) Assignee: Victoria Hand Project, Victoria (CA)

( * ) Notice: Subject to any disclaimer, the term of this patent is extended or adjusted under 35 U.S.C. 154(b) by 51 days.

(21) Appl. No.: 17/514,618

(22) Filed: Oct. 29, 2021

(65) Prior Publication Data

US 2022/0133508 A1    May 5, 2022

Related U.S. Application Data

(60) Provisional application No. 63/107,358, filed on Oct. 29, 2020.

(51) Int. Cl.
*A61F 2/54* (2006.01)
*A61F 2/50* (2006.01)
(Continued)

(52) U.S. Cl.
CPC ............ *A61F 2/586* (2013.01); *A61F 2/5046* (2013.01); *A61F 2/582* (2013.01);
(Continued)

(58) Field of Classification Search
CPC ........ A61F 2/586; A61F 2/5046; A61F 2/582; A61F 2002/543; A61F 2002/546; A61F 2002/587
See application file for complete search history.

(56) References Cited

U.S. PATENT DOCUMENTS

| 42,515 A | 4/1864 | Spellerberg |
| 51,238 A | 11/1865 | Spellerberg |

(Continued)

FOREIGN PATENT DOCUMENTS

| CN | 105056544 A | 11/2015 |
| DE | 102012012173 | 3/2014 |

(Continued)

OTHER PUBLICATIONS

U.S. Appl. No. 17/514,618, filed Oct. 29, 2021, Nikolai Dechev.
(Continued)

*Primary Examiner* — Bruce E Snow

(57) ABSTRACT

Low-cost prosthetic apparatus, methods, kits, and systems with improved force transfer elements are disclosed. For example, the prosthetic apparatus may comprise: a plurality of first components manufactured from a first material to define 3D shapes with exterior surfaces resembling digits of a human hand; and a plurality of second components manufactured from a second material to define 2D shapes that are rotatably engageable with the 3D shapes to define force transfer elements operable to close the digits around an object responsive to a pull force applied to the force transfer elements, wherein the first material is different from the second material. Methods for manufacturing and assembling prosthetic apparatus also are disclosed along with related kits and systems.

23 Claims, 24 Drawing Sheets

(51) Int. Cl.
*A61F 2/58* (2006.01)
*A61F 2/68* (2006.01)

(52) U.S. Cl.
CPC ... *A61F 2002/543* (2013.01); *A61F 2002/546* (2013.01); *A61F 2002/587* (2013.01); *A61F 2002/6836* (2013.01)

(56) References Cited

U.S. PATENT DOCUMENTS

| | | | |
|---|---|---|---|
| 1,225,415 A | 5/1917 | Cronemiller |
| 1,247,077 A | 11/1917 | Caron |
| 1,273,461 A | 7/1918 | Corley |
| 1,298,502 A | 3/1919 | Henning |
| 1,324,564 A | 12/1919 | Pringle |
| 1,347,004 A | 7/1920 | Conrad |
| 1,365,646 A | 1/1921 | Charles |
| 1,366,453 A | 1/1921 | Henning |
| 1,385,817 A | 7/1921 | Grand |
| 1,402,709 A | 1/1922 | Albert |
| 1,458,923 A | 6/1923 | Mackenzie |
| 1,465,933 A | 8/1923 | Charles |
| 1,466,163 A | 8/1923 | Harris |
| 1,484,913 A | 2/1924 | Meredith |
| 1,507,681 A | 9/1924 | Alberto et al. |
| 1,507,683 A | 9/1924 | Alberto et al. |
| 1,569,286 A | 1/1926 | Edward |
| 1,630,277 A | 5/1927 | James |
| 1,644,833 A | 10/1927 | George |
| 1,742,269 A | 1/1930 | Mcelroy |
| 1,792,183 A | 2/1931 | Alberto |
| 1,989,960 A | 2/1935 | Wheeler et al. |
| 2,285,885 A | 6/1942 | Becker |
| 2,287,781 A | 6/1942 | Carnes |
| 2,301,009 A | 11/1942 | Becker |
| 2,364,313 A | 12/1944 | Pecorella |
| 2,425,154 A | 8/1947 | Hibbard |
| 2,433,301 A | 12/1947 | Simpson |
| 2,457,305 A | 12/1948 | Dale |
| 2,464,577 A | 3/1949 | Walter |
| 2,493,776 A | 1/1950 | Alberto et al. |
| 2,516,791 A | 7/1950 | Motis et al. |
| 2,532,732 A | 12/1950 | Sansbury |
| 2,535,489 A | 12/1950 | Edwards |
| 2,537,551 A | 1/1951 | Sansbury |
| 2,540,374 A | 2/1951 | Motis |
| 2,540,375 A | 2/1951 | Motis |
| 2,549,716 A | 4/1951 | Harold |
| 2,549,792 A | 4/1951 | Fletcher |
| 2,553,827 A | 5/1951 | Mason |
| 2,553,830 A | 5/1951 | Motis |
| 2,556,524 A | 6/1951 | Drennon |
| 2,561,383 A | 7/1951 | Larkins et al. |
| 2,572,914 A | 10/1951 | Chapman et al. |
| 2,582,234 A | 1/1952 | Conzelman et al. |
| 2,592,842 A | 4/1952 | Alderson |
| 2,626,398 A | 1/1953 | Grindle et al. |
| 2,652,570 A | 9/1953 | John |
| 2,654,891 A | 10/1953 | Robinson |
| 2,669,727 A | 2/1954 | Theodore |
| 2,706,296 A | 4/1955 | Fletcher et al. |
| 2,847,678 A | 8/1958 | Theodore |
| 2,853,711 A | 9/1958 | Becker |
| 2,859,450 A | 11/1958 | Becker |
| 2,867,819 A | 1/1959 | George |
| 2,885,686 A | 5/1959 | Giaimo |
| 3,026,534 A | 3/1962 | Brown |
| 3,107,358 A | 10/1963 | Prout |
| 3,159,847 A | 12/1964 | Prout |
| 3,258,784 A | 7/1966 | Brown |
| 3,382,506 A | 5/1968 | William et al. |
| 3,413,658 A | 12/1968 | Becker |
| 3,432,198 A | 3/1969 | Connor |
| 3,694,021 A | 9/1972 | Mullen |
| 4,038,706 A | 8/1977 | Ober et al. |
| 4,040,130 A | 8/1977 | Laure |
| 4,067,070 A | 1/1978 | Seamone et al. |
| 4,074,367 A | 2/1978 | Loveless |
| 4,084,267 A | 4/1978 | Zadina |
| 4,094,016 A | 6/1978 | Eroyan |
| 4,167,044 A | 9/1979 | Girard |
| 4,180,870 A | 1/1980 | Radulovic et al. |
| 4,232,405 A | 11/1980 | Janovsky |
| 4,291,421 A | 9/1981 | Massey et al. |
| 4,310,932 A | 1/1982 | Nader et al. |
| 4,364,593 A | 12/1982 | Maeda |
| 4,521,924 A | 6/1985 | Jacobsen et al. |
| 4,604,098 A | 8/1986 | Seamone et al. |
| 4,651,719 A | 3/1987 | Funk et al. |
| 4,685,924 A | 8/1987 | Massey |
| 4,685,928 A | 8/1987 | Yaeger |
| 4,685,929 A | 8/1987 | Monestier |
| 4,792,338 A | 12/1988 | Rennerfelt |
| 4,865,613 A | 9/1989 | Rizzo |
| 4,921,293 A | 5/1990 | Ruoff et al. |
| 4,946,380 A | 8/1990 | Lee |
| 4,957,281 A | 9/1990 | Christolear, Jr. |
| 4,990,162 A | 2/1991 | LeBlanc et al. |
| 5,080,682 A | 1/1992 | Schectman |
| 5,104,121 A | 4/1992 | Webb |
| 5,314,500 A | 5/1994 | Weddendorf |
| 5,800,571 A | 9/1998 | Carlson et al. |
| 5,800,572 A | 9/1998 | Loveall |
| 5,888,235 A | 3/1999 | Jacobsen et al. |
| 6,115,898 A | 9/2000 | Sawdon |
| 6,513,198 B2 | 2/2003 | Lu |
| 6,896,704 B1 | 5/2005 | Higuchi et al. |
| 6,913,627 B2 | 7/2005 | Matsuda |
| 7,087,092 B1 | 8/2006 | Landsberger |
| 7,112,221 B2 | 9/2006 | Harris |
| 7,361,197 B2 | 4/2008 | Winfrey |
| 7,655,051 B2 | 2/2010 | Stark |
| 7,867,287 B2 | 1/2011 | Puchhammer |
| 8,132,291 B2 | 3/2012 | Tsai et al. |
| 8,343,234 B2 | 1/2013 | Puchhammer |
| 8,608,398 B2 | 12/2013 | Mekid |
| 8,684,621 B2 | 4/2014 | Forthaus et al. |
| 8,795,387 B1 | 8/2014 | Razink |
| 9,320,621 B2 | 4/2016 | Iversen et al. |
| 9,572,688 B2 | 2/2017 | Puchhammer et al. |
| 9,713,541 B2 * | 7/2017 | Thompson, Jr. ........ A61F 2/586 |
| 9,788,529 B2 | 10/2017 | Axelrod et al. |
| 10,219,919 B2 | 3/2019 | Belter et al. |
| 10,271,966 B2 | 4/2019 | Glasgow |
| 11,013,620 B2 | 5/2021 | Dechev et al. |
| 2005/0006915 A1 | 1/2005 | Matsuda |
| 2005/0021155 A1 | 1/2005 | Brimalm |
| 2006/0129248 A1 | 6/2006 | Stark |
| 2006/0224249 A1 | 10/2006 | Winfrey |
| 2007/0173955 A1 | 7/2007 | Archer et al. |
| 2007/0213842 A1 | 9/2007 | Simmons |
| 2008/0188952 A1 | 8/2008 | Veatch et al. |
| 2008/0262634 A1 | 10/2008 | Puchhammer |
| 2008/0262636 A1 | 10/2008 | Puchhammer |
| 2008/0319553 A1 | 12/2008 | Puchhammer |
| 2010/0274365 A1 | 10/2010 | Evans et al. |
| 2012/0146352 A1 | 6/2012 | Haslinger |
| 2012/0150322 A1 | 6/2012 | Goldfarb et al. |
| 2013/0046395 A1 | 2/2013 | Mcleary |
| 2014/0171846 A1 | 6/2014 | Bonutti et al. |
| 2015/0230941 A1 | 8/2015 | Jury |
| 2015/0297367 A1 | 10/2015 | Baba et al. |
| 2015/0351935 A1 | 12/2015 | Donati et al. |
| 2016/0166409 A1 | 6/2016 | Goldfarb et al. |
| 2016/0374833 A1 | 12/2016 | Dechev et al. |
| 2017/0049583 A1 | 2/2017 | Belter et al. |
| 2018/0098862 A1 | 4/2018 | Kuiken et al. |
| 2018/0133028 A1 | 5/2018 | Poirters |
| 2018/0140441 A1 | 5/2018 | Poirters |

(56) References Cited

U.S. PATENT DOCUMENTS

| | | | |
|---|---|---|---|
| 2018/0311827 | A1 | 11/2018 | Bicchi et al. |
| 2022/0054283 | A1* | 2/2022 | Thompson, Jr. ........ A61F 2/586 |

FOREIGN PATENT DOCUMENTS

| | | |
|---|---|---|
| DE | 102015116133 | 1/2017 |
| EP | 0079593 B1 | 2/1986 |
| EP | 0635247 B1 | 11/1998 |
| EP | 1457294 A4 | 9/2006 |
| FR | 2665833 A1 | 2/1992 |
| GB | 157256 A | 6/1921 |
| GB | 2278281 A | 11/1994 |
| JP | 2014213199 A | 11/2014 |
| KR | 101738098 B1 | 5/2017 |
| SU | 409715 A1 | 1/1974 |
| WO | 1985001437 A1 | 4/1985 |
| WO | 2000071060 A1 | 11/2000 |
| WO | 2003017880 A1 | 3/2003 |
| WO | 2007076763 A2 | 7/2007 |
| WO | 2012021823 A1 | 2/2012 |
| WO | 2013076683 A1 | 5/2013 |
| WO | 2013185231 A1 | 12/2013 |
| WO | 2017111582 A1 | 6/2017 |
| WO | 2017212128 A1 | 12/2017 |

OTHER PUBLICATIONS

Angie MacDonald, Changing lives in developing countries with 3D printed prosthetics, Nov. 22, 2016, 8 pages, Ultimaker.

Colin Pischke, "Victoria Hand Project—Guest Post", Pym3d, Mar. 19, 2017, 3 pages, available at: https://www.printyourmind3d.ca/blogs/articles/victoria-hand-project (last accessed: Feb. 15, 2022).

Cormac O'Brien, "Victoria Hand Project gets tapped for half-million-dollar grant", Martlet, Mar. 23, 2017, 6 pages, available at: https://www.martlet.ca/victoria-hand-project-gets-tapped-for-half-million-dollar-grant/ (last accessed: Feb. 15, 2022).

Dechev et al., "Multiple Finger, Passive Adaptive Grasp Prosthetic Hand," Journal of Mechanism and Machine Theory, 2001, pp. 1157-1173, vol. 36, Elsevier Science Ltd.

Hanna Watkin, "The Victoria Hand Project Uses 3D Printing to Create Ergonomic Prosthetics", All3DP, Dec. 8, 2016, 5 pages, available at: https://all3dp.com/the-victoria-hand-project-uses-3d-printing-to-create-ergonomic-prosthetics/ (last accessed: Feb. 15, 2022).

Jeffrey Joiner, "Guidelines for the design of electromechanical hands and incorporation of compliant fingertips", 1994, National Library of Canada, Ottawa, Canada.

Lisa O'Brien, "The Winston Churchill Memorial Trust of Australia", The Winston Churchill Memorial Trust, Jun. 9, 2018, 28 pages.

Neeta Garcha, "Lending a helping hand: Victoria non-profit in the running for huge Google grant", Global News, Mar. 9, 2017, 8 pages, available at: https://globalnews.ca/news/3297918/lending-a-helping-hand-victoria-non-profit-in-the-running-for-huge-google-grant/?fbclid=IwAR3MKus2OyMXLE7HoAQpbeMz4rXKZRO9CFvKkigomal1lesWX9pPuF2CPxo (last accessed: Feb. 15, 2022).

Nick Dechev, "Victoria Hand Project Info Video", Vimeo, Jul. 14, 2015, 2 pages, available at: https://vimeo.com/133500986 (last accessed: Feb. 15, 2022).

"MyolinoWrist 2000," Ottobock, Est. Pub. Date. 2013, 3 pages, available at: https://shop.ottobock.us/Prosthetics/Upper-Limb-Prosthetics/Myo-Hands-and-Components/Myo-Wrist-Units-and-Rotation/MyolinoWrist-2000/p/10V51~52#product-documents-section (last accessed: Feb. 15, 2022).

Sarah Anderson Goehrke, "Victoria Hand Project—Offering Advanced, Affordable 3D Printed Upper-Limb Prostheses", 3dprint.com, Jul. 13, 2015, 6 pages, available at: https://3dprint.com/80946/victoria-hand-project/ (last accessed: Feb. 15, 2022).

Susan Hall, "Victoria Hand Project: Applying 3D Printing to Prosthetics", The New Stack, Jun. 21, 2018, 13 pages, available at: https://thenewstack.io/victoria-hand-project-applying-3d-printing-to-prosthetics/ (last accessed: Feb. 15, 2022).

"The Raptor Hand", Enabling The Future, Est. Pub. Date: Sep. 29, 2015, 12 pages, available at: https://enablingthefuture.org/upper-limb-prosthetics/the-raptor-hand/ (last accessed: Feb. 15, 2022).

"The Victoria Hand Project: Making a World of Difference ~Nick Dechev, Ph.D.", The Canadian Club of Victoria, Mar. 16, 2017, 4 pages, available at: https://thecanadianclubofvictoria.com/event/test2/ (last accessed: Feb. 15, 2022).

Travis Paterson, "3D printers make Victoria Hand Project a reality", Victoria News, Nov. 10, 2017, 3 pages, available at: https://www.vicnews.com/news/3d-printers-make-victoria-hand-project-a-reality/?fbclid=IwAR21xxhqVnkPBM1BqWaGdF0qYwGhRkHH31edrCuTs5Tam_Hmpkr3peJiTO4 (last accessed: Feb. 15, 2022).

Vichandproject, Instagram, Jul. 4, 2017, available at: https://www.instagram.com/p/BWIqE9_FpAw/?utm_source=ig_web_copy_link (last accessed: Feb. 15, 2022).

Victoria Hand Project, "Victoria Hand Project—Fundraiser for Canadian Amputees (Jan. 2018)", YouTube, Jan. 15, 2018, available at: https://www.youtube.com/watch?v=fMnj6KLqZ-U (last accessed: Feb. 15, 2022).

Annick Mottard. Underactuated tendon-driven robotic/prosthetic hands: design issues. Robotics Proceedings (2017), https://www.roboticsproceedings.org/rss13/p19.pdf (Accessed Jul. 21, 2023).

Bethanylc, E-Nable: How to Assemble the Isabella Arm by FATHOM, 30 pages, URL: https://www.instructables.com/id/E-NABLE-How-to-assemble-the-Isabella-Arm-by-FATHOM/, Oct. 16, 2015 (Accessed Jul. 21, 2023).

Bob Radcoy, TRS Product Catalog (2015), http://www.trsprosthetics.com/wp-content/uploads/2015/10/TRS_CAT15-en.pdf (Accessed Jul. 21, 2023).

Christian Silva, 3D printed Mechanical Arm Enable Promimetic Fabrilab, Youtube (Sep. 11, 2017), https://www.youtube.com/watch?v=HS8D0MYCDKg (Accessed Jul. 21, 2023).

Christine Van Reeuwyk, UVic project rebuilds lives one hand at a time, Oak Bay News (Mar. 17, 2017), https://www.oakbaynews.com/news/uvic-project-rebuilds-lives-one-hand-at-a-time-448414 (Accessed Jul. 21, 2023).

CTV News Vancouver Island, UVic Engineers 3D-Print New Hand for Sidney man, CTV (date unknown) https://vancouverisland.ctvnews.ca/video?clipId=971219&fbclid=IwAR2d2-NmaSOkzhWc4dkJJZttOtuDB_FMMm4T2feAXEn0Y2V_usOHN86dP60 (Accessed Jul. 21, 2023).

Cuellar et al., Ten guidelines for the design of non-assembly mechanisms: The case of 3D-printed prosthetic hands, Proceedings of the Institution of Mechanical Engineers, Part H: Journal of Engineering in Medicine, 10, vol. 232, Issue 9, (2018), https://journals.sagepub.com/doi/epub/10.1177/0954411918794734 (Accessed Jul. 21, 2023).

De Laurentis et al., Mechanical Design of a Shape Memory Alloy Actuated Prosthetic Hand (2002), http://engineering.nyu.edu/mechatronics/Control_Lab/bck/Padmini/Nano/Mavroidis/THC.pdf (Accessed Jul. 21, 2023).

E-NABLE, Volunteers offer prosthetic hands made for children by 3D printers, Youtube (2014)https://www.youtube.com/watch?v=T9nngOrdPkg (Accessed Jul. 21, 2023).

Enabling the Future, The Limbless Arm, http://enablingthefuture.org/upper-limb-prosthetics/the-limbitless-arm/, (Accessed Jul. 21, 2023).

Enabling the Future, The Rit Arm, http://enablingthefuture.org/upper-limb-prosthetics/rit-arm/ (Accessed Jul. 21, 2023).

John Diamond, How a Whippletree works in an e-NABLE hand, Youtube (2014)https://www.youtube.com/watch?v=dW5B_CeJtd8 (Accessed Jul. 21, 2023).

Justine Hunter, Forging prosthetics from plastic for a pittance, The Globe and Mail (Dec. 28, 2016) https://www.theglobeandmail.com/news/british-columbia/victoria-hand-project-is-forging-prosthetics-from-plastic-for-a-pittance/article33444630/?fbclid=IwAR3Xi-t3U9DwQt7gLEMdpZf2S2_xhWAo7DvlAmKX2sNbs3IzoP05dk6tK5U (Accessed Jul. 21, 2023).

(56) References Cited

OTHER PUBLICATIONS

Kelly Knights. A Helping Hand to Those in Need-Improving the World with 3D Printing. 3D Heals blog (Jan. 13, 2019), https://3dheals.com/improving-the-world-with-3d-printing/ (Accessed Jul. 21, 2023).
Thinigverse, The Raptor Hand by e-NABLE, http://www.thingiverse.com/thing:476403 (Accessed Jul. 21, 2023).
Vichandproject, This is César, an amputee from Ecuador, Instagram (Mar. 8, 2017), https://www.instagram.com/p/BRYrghjFfl4/?utm_source=ig_web_copy_link (Accessed Jul. 21, 20123).
Vichandproject, With just over a month left in our Generosity Campaign, we still need your help to reach our goal of fitting 20 Canadian Amputees with our Victoria Hand, Instagram (Feb. 26, 2018), https://www.instagram.com/p/BfrsW24I2gn/?utm_source=ig_web_copy_link (Accessed Jul. 21, 2023).
Victoria Hand Project, #throwbackthurday to when Rick Mercer stopped by to visit our headquarters, Facebook (Nov. 30, 2017), https://www.facebook.com/victoriahandproject/posts/1917910715139451 (Accessed Jul. 21, 2023).
Victoria Hand Project, Amazing work with Range of Motion Project in Ecuador fitting Victoria Hand Prosthesis!, Facebook (Oct. 12, 2016), https://www.facebook.com/victoriahandproject/photos/a.1584810318449494/1731835533746971/ (Accessed Jul. 21, 2023).
Victoria Hand Project, Awesome work by Brent Wright and the LifeNabled, Inc. team for fitting Veronica with the Victoria Hand in Guatemala!, Facebook (Aug. 30, 2019), https://www.facebook.com/victoriahandproject/posts/2310895742507611 (Accessed Jul. 21, 2023).
Victoria Hand Project, Because the Victoria Hand is designed to mimic a hand as closely as possible, it can help amputees carry out the everyday tasks we take for granted, Facebook (Feb. 2, 2017), https://www.facebook.com/victoriahandproject/photos/a.1584810318449494/1782448592018998/ (Accessed Jul. 21, 2023).
Victoria Hand Project, Bishu Fitted With The Victoria Hand, Facebook ( Mar. 27, 2017), https://www.facebook.com/victoriahandproject/photos/a.1584810318449494/1806202796310244/ (Accessed Jul. 21, 2023).
Victoria Hand Project, Evolution of The Victoria Hand, Facebook (Mar. 24, 2017) https://www.facebook.com/victoriahandproject/photos/a.1584810318449494/1804903939773463/ (Accessed Jul. 21, 2023).
Victoria Hand Project, Features of the Victoria Hand and how it works!, Youtube (2018), https://www.youtube.com/watch?v=sUXGkAYWEa0 (Accessed Jul. 21, 2023), illegible copy.
Victoria Hand Project, Here is Mukta learning how to use his new VO200 hands, Facebook (Nov. 28, 2018), https://www.facebook.com/victoriahandproject/posts/2088954921368362 (Accessed Jul. 21, 2023).
Victoria Hand Project, Here's a little throwback to when VHP visited Cambodia in June of 2016, Facebook (Jan. 25, 2018), https://www.facebook.com/victoriahandproject/posts/1944350352495487 (Accessed Jul. 21, 2023).
Victoria Hand Project, Here's a little throwback to when VHP visited Cambodia in June of 2016., Facebook (Jan. 25, 2018), https://www.facebook.com/victoriahandproject/posts/1962961727301016 (Accessed Jul. 21, 2023).
Victoria Hand Project, If you've been following our Instagram page, then you might recognize this face, Facebook (Dec. 16, 2017), https://www.facebook.com/victoriahandproject/posts/1923540691243120 (Accessed Jul. 21, 2023).
Victoria Hand Project, Mohamed recently lost his arm in a motorcycle accident, Facebook (Dec. 13, 2017), https://www.facebook.com/victoriahandproject/posts/1923538287910027 (Accessed Jul. 21, 2023).
Victoria Hand Project, One Hand Challenge!, Youtube (2015), https://www.youtube.com/watch?v=a6E2Tr7Bprg (Accessed Jul. 21, 2023).
Victoria Hand Project, One of our missions here at Victoria Hand Project is to make a positive impact worldwide, Facebook (Nov. 15, 2017), https://www.facebook.com/victoriahandproject/posts/1910947722502417 (Accessed Jul. 21, 2023).
Victoria Hand Project, Our 3D printed upper-limbs open up a wealth of opportunities for our users all over the world, Facebook (Nov. 18, 2017), https://www.facebook.com/victoriahandproject/posts/1911761752421014 (Accessed Jul. 21, 2023).
Victoria Hand Project, Recently a local charity from Nanaimo, Canada, Kids International Development Society, reached out to us to see if we could fit Vanna with the Victoria Hand, Facebook (Jul. 29, 2019), https://www.facebook.com/victoriahandproject/posts/2288946058035913 (Accessed Jul. 21, 2023).
Victoria Hand Project, Remember when Rick Mercer visited VHP back in November ??, Facebook (Jan. 16, 2018), https://www.facebook.com/victoriahandproject/posts/1939847636279092 (Accessed Jul. 21, 2023).
Victoria Hand Project, Thanks again to Rick Mercer Report for coming out and checking out our operation, Facebook (Nov. 16, 2017), https://www.facebook.com/victoriahandproject/posts/1911363212460868 (Accessed Jul. 21, 2023).
Victoria Hand Project, The Making of the Victoria Hand: A Functional, Low-Cost Prosthesis, Youtube (2016), https://www.youtube.com/watch?v=9Rkf-K7oylw (Accessed Jul. 21, 2023).
Victoria Hand Project, Through collaboration with international partners and medical facilities, VHP has made an impact in countries across the world, Facebook (Jan. 4, 2018), https://www.facebook.com/victoriahandproject/posts/1934287786835077 (Accessed Jul. 21, 2023).
Victoria Hand Project, Using feedback from our clinical partners around the world, we have identified a need for a system that fits people with transhumeral amputations, Facebook (Aug. 11, 2017), https://www.facebook.com/victoriahandproject/posts/1870329629897560 (Accessed Jul. 21, 2023).
Victoria Hand Project, VHP Updated Cover Photo (Jul. 11, 2015), https://www.facebook.com/victoriahandproject/posts/1583265998603926 (Accessed Jul. 21, 2023).
Victoria Hand Project, Victoria Hand 3D Printed Prosthetic, Youtube (Jul. 10, 2015), https://www.youtube.com/watch?v=t0ozZqQH5N8 (Accessed Jul. 21, 2023).
Victoria Hand Project, Victoria Hand Project 3D Printed Prosthetic Haiti & Cambodia, Youtube (Sep. 9, 2016), https://www.youtube.com/watch?v=YhhtMGKA-zs (Accessed Jul. 22, 2023).
Victoria Hand Project, Victoria Hand Project 3D Printed Prosthetic, Youtube (Feb. 17, 2016) https://www.youtube.com/watch?v=uSd9uxlc5Sw (Accessed Jul. 22, 2023).
Victoria Hand Project, Victoria Hand Project Guatemala, Youtube (Sep. 9, 2016), https://www.youtube.com/watch?v=rVIePGFRcel (Accessed Jul. 22, 2023).
Victoria Hand Project, Victoria Hand Project: 3D Printed Prostheses for Guatemala and Nepal, Youtube (Jul. 22, 2015), https://www.youtube.com/watch?v=cIVHWrOACTk (Accessed Jul. 22, 2023).
Victoria Hand Project, We are excited to announce that VHP has recently created our own Patreon account!, Facebook (Jul. 25, 2019) https://www.facebook.com/victoriahandproject/posts/2286333854963800 (Accessed Jul. 21, 2023).
Victoria Hand Project, We are happy to announce after lots of work the VC200 hand has been completed and will soon be deployed to our partner countries, Facebook (Jul. 4, 2017), https://www.facebook.com/victoriahandproject/posts/1852565468340643 (Accessed Jul. 21, 2023).
Victoria Hand Project, We are proud to announce 12 Victoria Hands will be deployed in Guatemala, Facebook (Oct. 6, 2017), https://www.facebook.com/victoriahandproject/posts/1893825434214646 (Accessed Jul. 21, 2023).
Victoria Hand Project, We have another trip we are excited to announce!, Facebook (Mar. 15, 2018), https://www.facebook.com/victoriahandproject/posts/1968932906703898 (Accessed Jul. 21, 2023).
Victoria Hand Project, With all six of the infinity gems, the world is in the palm of your hand, Facebook (Oct. 31, 2018), https://www.facebook.com/victoriahandproject/photos/a.1584810318449494/2120401051557082/ (Accessed Jul. 21, 2023).
Victoria Hand Project, Youssef recently received a Victoria Hand by the Canadian-Egyptian Hand (CEH) project in Cairo Egypt (May

(56) References Cited

OTHER PUBLICATIONS 18, 2019), https://www.facebook.com/victoriahandproject/posts/2238776629719523 (Accessed Jul. 21, 2023).

* cited by examiner

400

410: ASSEMBLING A FINGER DIGIT ASSEMBLY.

420: ASSEMBLING A SLIDER FRAME ASSEMBLY.

430: ASSEMBLING A THUMB DIGIT ASSEMBLY.

440: ASSEMBLING THE FINGER DIGIT ASSEMBLY TOGETHER WITH THE SLIDER FRAME ASSEMBLY, THE THUMB DIGIT ASSEMBLY, AND A HAND BODY.

FIG. 20

LOW-COST PROSTHETIC APPARATUS, METHODS, KITS, AND SYSTEMS WITH IMPROVED FORCE TRANSFER ELEMENTS

CROSS-REFERENCE TO RELATED APPLICATIONS

This patent application claims the benefit of priority under 35 U.S.C. § 119 to U.S. Provisional Patent Application No. 63/107,358, filed Oct. 29, 2020, the entirety of which is hereby incorporated by reference.

BACKGROUND

Field

Aspects of the present disclosure generally relate to low-cost prosthetic apparatus, methods, kits, and systems. Particular aspects comprise improved force transfer elements manufactured from different materials.

Description of Related Art

Various prosthetics arms and hands are available to help people with a partial limb replace some lost anatomical or body functions. There are many different prosthetic arms and prosthetic hands available to amputees, ranging in price and providing various functions. The two most common types of prosthetic arms are mechanical arms and myoelectric arms, both of which may comprise a prosthetic hand such as a prosthetic hook. Most mechanical arms that have no electric or electronic components, and instead utilize a motion of the amputee to actuate the prosthetic hand, usually in conjunction with a harness worn on the amputee's body. Most myoelectric arms utilize a combination of sensors and actuators to activate the prosthetic hand, making them more expensive than mechanical arms.

Both types of prosthetic arms, mechanical and myoelectric, can be expensive to manufacture with conventional manufacturing methods (e.g., molding or stamping) because they often have parts that are difficult to produce economically in small batch quantities, making it hard to amortize the costs of producing the parts. Conventional manufacturing methods also require specialized equipment that may not be available in many parts of the world. One advantage of these conventional methods is that they can produce strong parts. Alternative lower-cost methods of making prosthetic arms and prosthetic hands are known, such as additive methods like 3D printing, but they typically require base materials that are of lower strength than the base materials used by conventional manufacturing methods.

SUMMARY

Aspects of the present disclosure relate to low-cost prosthetic apparatus, methods, kits, and systems with improved force transfer elements. Numerous exemplary aspects of the present disclosure are now described.

One aspect of this disclosure is a prosthetic apparatus. For example, the prosthetic apparatus may comprise: a plurality of first components manufactured from a first material to define 3D shapes with exterior surfaces resembling digits of a human hand; and a plurality of second components manufactured from a second material to define 2D shapes that are rotatably engaged with the 3D shapes to define force transfer elements operable to close the digits around an object responsive to a pull force applied to the force transfer elements, wherein the first material is different from the second material.

The 3D shapes of the plurality of first components may be manufactured from the first material with an additive manufacturing method. The first material may be 3D-printable. For example, the 3D shapes of the plurality of first components may be manufactured from the first material with a 3D printer. The first material may comprise a polymeric material, such as a polymer or a thermal polymer. The plurality of second components may be manufactured from the second material with a rapid manufacturing method. For example, the plurality of second components may be cut from a sheet of the second material using a laser cutter or a water jet cutter. The second material may comprise a metallic material, such as stainless steel or titanium.

The 2D shape of one second component of the plurality of second components may be foldable into an additional 3D shape of the force transfer elements. The 2D shapes of at least two second components of the plurality of second components may be engageable with one another to define an additional 3D shape of the force transfer elements. The plurality of second components may have a uniform thickness. For example, the uniform thickness may be between approximately 0.5 mm and approximately 5 mm. As a further example, the uniform thickness may less than approximately 5 mm. The force transfer elements may be operable to close the digits around the object with an adaptive grasp. The apparatus may comprise one or more springs operable to bias the digits toward an open position of the adaptive grasp. A weight of the plurality of second components may comprise between approximately 5% and approximately 25% of a total weight of the prosthetic apparatus. The 2D shapes may be rotatably engaged with the 3D shapes, such as with a pin connection.

The plurality of first components may be 3D printed with the first material using 3D printing data associated with a human subject. The plurality of second components may be cut from the second material using 2D cutting data associated with the human subject. The plurality of second components may be cut from a single plate of the second material using the 2D cutting data. The plurality of second components may be removably attached to the single plate by frangible portions after being cut from the single plate. A rectangular cross-section of one second component of the plurality of second components may be receivable in an opening of another second component of the plurality of second components, such as a circular opening. The apparatus may comprise one or more springs operable with the plurality of first components to bias the digits toward an open position. Structural characteristics of the first material may be different from those of the second material. For example, a stress carried by the plurality of second components when actuating the apparatus may be greater than an ultimate tensile stress of the first material.

The plurality of first components may comprise a 3D thumb shape with exterior surfaces resembling a thumb of human hand. The plurality of second components may comprise 2D operational shapes that are engageable with the 3D thumb shape to define an operational linkage operable to close the thumb responsive to the pull force. The 2D operational shapes may comprise a thumb link that is fixedly engageable with the 3D thumb shape and operable to transfer the pull force from the operational linkage to the 3D thumb shape.

Another aspect of this disclosure is a kit. For example, the kit may comprise: a plurality of first components manufactured from a first material to define 3D shapes with exterior surfaces resembling digits of a human hand; a plurality of second components manufactured from a second material to define 2D shapes that are rotatably engaged with the 3D shapes to define force transfer elements operable to close the digits around an object responsive to a pull force applied to the force transfer elements, wherein the first material is different from the second material; a plurality of engagement elements; and instructions for rotatably engaging the plurality of first components with the plurality of second components using the plurality of engagement elements. The kit also may comprise any variations of any prosthetic apparatus described herein.

Yet another aspect of this disclosure is a system. For example, the system may comprise: an upper arm prosthetic engageable with a partial limb; and a lower arm prosthetic engageable with a prosthetic apparatus comprising a plurality of first components manufactured from a first material to define 3D shapes with exterior surfaces resembling digits of a human hand, and a plurality of second components manufactured from a second material to define 2D shapes that are rotatably engaged with the 3D shapes to define force transfer elements operable to close the digits around an object responsive to a pull force applied to the force transfer elements, wherein the first material is different from the second material. In this example, the plurality of first components may define additional 3D shapes with exterior surfaces resembling a human elbow and the plurality of second components may define additional 2D shapes that are rotatably engageable with the additional 3D shapes to define additional force transfer elements operable to selectively move the upper arm prosthetic relative to the lower arm prosthetic. The system also may comprise any variations of any prosthetic apparatus described herein.

The additional force transfer elements may comprise a one-way pawl and ratchet mechanism and a release for the one-way pawl and ratchet mechanism. For example, the one-way pawl and ratchet mechanism may comprise a ratchet engaged with the upper arm prosthetic and a pawl engaged with the lower arm prosthetic so that lifting the lower arm prosthetic causes the ratchet to rotate and engage the pawl to prevent the lower arm prosthetic portion from lowering. The 3D shapes and/or the additional 3D shapes of the plurality of first components may be 3D printed with the first material. The 2D shapes and/or the additional 2D shapes of the plurality of second components may be cut from the second material. For example, the 2D shapes and/or the additional 2D shapes of the plurality of second components may be cut from a single sheet of the second material.

BRIEF DESCRIPTION OF THE DRAWINGS

The accompanying drawings, which are incorporated in and constitute part of this disclosure, illustrate exemplary aspects that, together with the written descriptions, serve to explain the principles of this disclosure. Numerous aspects are particularly described, pointed out, and taught in the written descriptions. Some structural and operational aspects may be even better understood by referencing the written portions together with the accompanying drawings, of which:

FIG. 20 depicts another exemplary assembly method.

DETAILED DESCRIPTION

Figure 1:
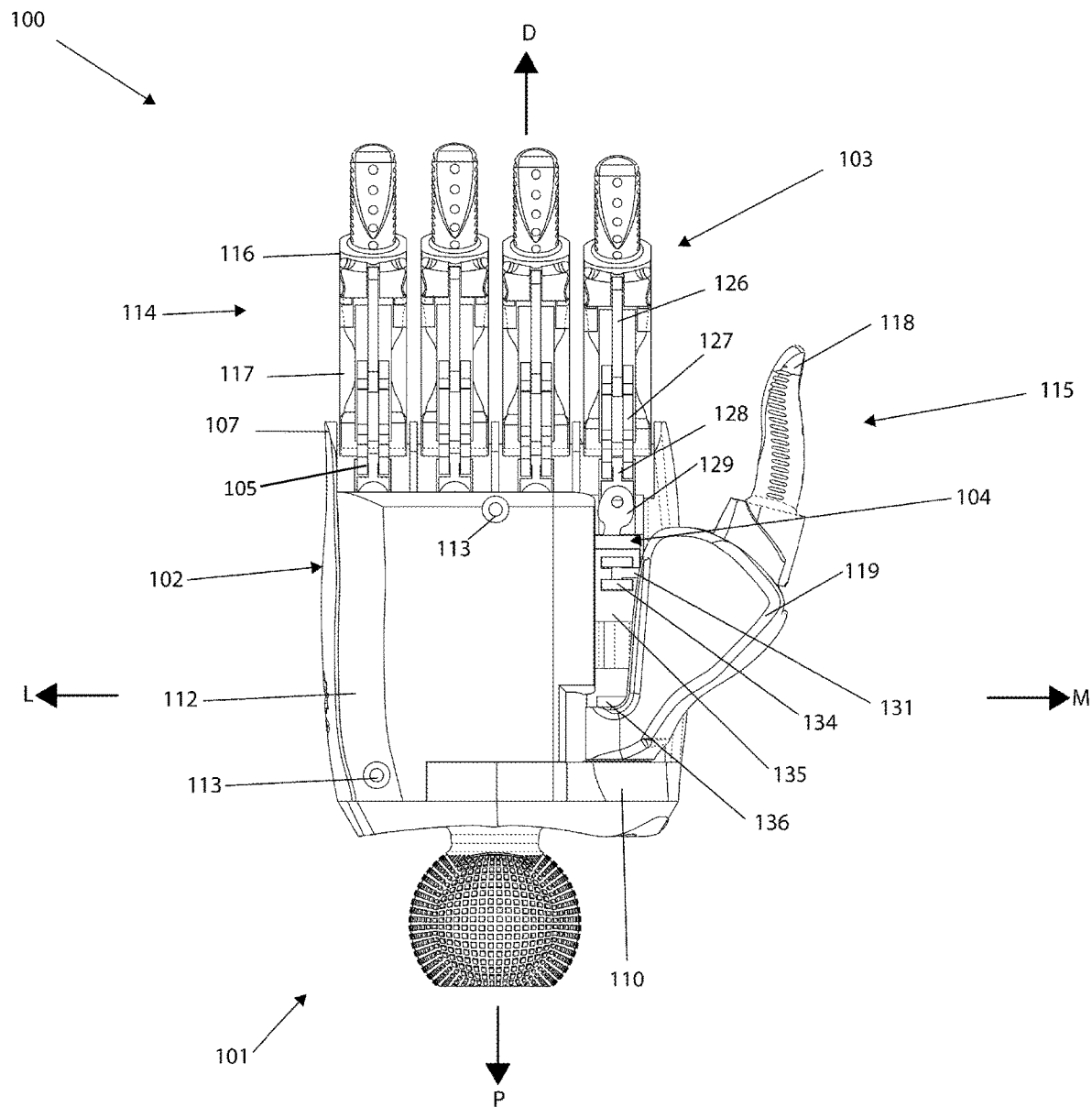
FIG. 1 depicts a palm facing view of an exemplary prosthetic hand apparatus.

Aspects of the present disclosure are not limited to the exemplary structural details and component arrangements described in this description and shown in the accompanying drawings. Many aspects of this disclosure may be applicable to other aspects and/or capable of being practiced or carried out in various variants of use, including the examples described herein.

Throughout the written descriptions, specific details are set forth in order to provide a more thorough understanding to persons of ordinary skill in the art. For convenience and ease of description, some well-known elements may be described conceptually to avoid unnecessarily obscuring the focus of this disclosure. In this regard, the written descriptions and accompanying drawings should be interpreted as illustrative rather than restrictive, enabling rather than limiting.

Exemplary aspects of this disclosure reference various low-cost prosthetic apparatus, method, kits, and systems. Some aspects are described with reference to a particular type of prosthetic (e.g., a hand or arm) manufactured with a particular method (e.g., 3D printing and laser or water cutting) for operation by a particular user (e.g., humans) with a particular power source (e.g., the human body) to perform a particular function (e.g., grasping an object). Unless claimed, these exemplary aspects are provided for convenience and not intended to limit this disclosure. Accordingly, the concepts described in this disclosure may be utilized with any type of prosthetic apparatus, methods, kits, and systems operable by any user with any power source to perform any function, including the examples described herein.

Some aspects and relative arrangements thereof may be described relative to one or more reference axes. One axis may be non-parallel with another axis in some perspectives, meaning the axes extend across and/or intersect. The term "elongated" may describe any aspect having a length along one axis that is longer in relation to a width along another non-parallel axis. Additional axes, movements, and forces may be described with in relation to any reference axis. These axes are provided for convenience and do not limit this disclosure unless claimed.

Pairings of anatomical terms, such as "proximal" and "distal," "palmar" and "dorsal," and "medial" and "lateral" may be described in relation to a corresponding reference axis, such as a proximal-distal axis, a palmar-dorsal axis, and a medial-lateral axis. These pairings may orient some aspects relative to a partial limb of a human body. Proximal generally refers to directions and/or positions closer to the partial limb along the proximal-distal axis and distal generally refers to directions and/or positions away from the partial limb along the proximal-distal axis. Palmar generally refers to directions and/or positions closer to a palm facing side of the partial limb along the palmar-dorsal axis and dorsal generally refers to directions and/or positions away from the palm facing side of the partial limb along the palmar-dorsal axis. Medial generally refers to directions and/or positions closer to a midline plane of the partial limb along a medial-lateral axis and lateral generally refers to directions and/or positions away from the midline plane of the partial limb along the medial-lateral axis. For ease of description, a thumb of the partial limb is shown as medial of the midline plane and a pinky of the partial limb is shown as lateral of the midline plane. These anatomical terms are provided for convenience and not limiting unless claimed.

As shown in the drawings, proximal directions may be generally indicated on the proximal-distal axis by a directional arrow "P," distal directions may be generally indicated on the proximal-distal axis by a directional arrow "D," palmar directions may be generally indicated on the palmar-dorsal axis by a directional arrow "Pa," dorsal directions may be generally indicated on palmar-dorsal axis by a directional arrow "Do," medial directions may be generally indicated on the medial-lateral axis by a directional arrow "M," and lateral directions may be generally indicated on the medial-lateral axis by a directional arrow "L." Similar to above, these directional arrows are provided for convenience and not limiting unless claimed.

As used herein, inclusive terms such as "comprises," "comprising," "includes," "including," and variations thereof, are intended to cover a non-exclusive inclusion, such that any low-cost prosthetic apparatus, method, kit and system, or component(s) thereof described as comprising a list of elements does not include only those elements but may include other elements not expressly listed and/or inherent thereto. Unless stated otherwise, the term "exemplary" is used in the sense of "example" rather than "ideal." Various terms of approximation are used, including "approximately" and "generally." Approximately means "roughly" or within 10% of a stated outcome. Generally means "usually" or more than a 50% probability.

Terms such as "engageable with," "engaged with," and "engaging" are used in this disclosure to describe connections between two or more elements. Some connections may be non-removable and/or non-rotatable, such as when the two or more elements are formed together and cannot be rotated and/or separated without damage. Other connections may be removable and/or rotatable, such as when the two or more elements are coupled together by engagement elements (e.g., bolts, pins, rods, screws, etc.) and/or structural elements (e.g., joints, hinges, etc.) that may be rotated relative to one another and/or separated. The term "pin" is used as an exemplary engagement element and should be broadly interpreted to include any rotation-enabling structure, including those that are independent of or formed integral with another structure. Accordingly, unless stated otherwise, the term engageable and its equivalents should be broadly interpreted to comprise any such variations.

Aspects of an exemplary prosthetic apparatus embodied as a prosthetic hand apparatus 100 are now described. As shown in FIGS. 1-10, prosthetic hand apparatus 100 may comprise a plurality of components that are manufactured with low-cost manufacturing methods and assembled as described herein to help a human subject with a partial limb regain some normal functions. Some aspects of prosthetic hand apparatus 100 are described with reference to components made from completely different materials. At least two different materials may be assembled to make prosthetic hand apparatus 100. As shown in FIGS. 1-10, prosthetic hand apparatus 100 may be made from first components—e.g., the "polymeric components" described herein; second components—e.g., "metallic components" described herein; and engagement elements operable therewith—e.g., the various pins, rods, screws, and springs described herein.

The polymeric components of prosthetic hand apparatus 100 may comprise exterior surfaces that are shaped and colored to realize a particular outward appearance of a human hand and its digits, allowing them to be anatomically consistent with a human subject. As shown in FIGS. 1-10, the polymeric components may comprise complex 3D shapes manufactured with an additive manufacturing method, such as 3D printing, that allows prosthetic hand apparatus 100 to realize a high degree of anatomically consistency, such as a visually consistent match with a lost limb. The 3D printer may print the 3D shapes of the polymeric components from a printable base material responsive to 3D printing data. For example, the printable base material may comprise a thermoplastic such as acrylonitrile butadiene styrene (or "ABS") or polylactic acid ("or PLA"), both of which have desirable biocompatibility and strength characteristics. Any comparable base materials may be used.

Figure 17:
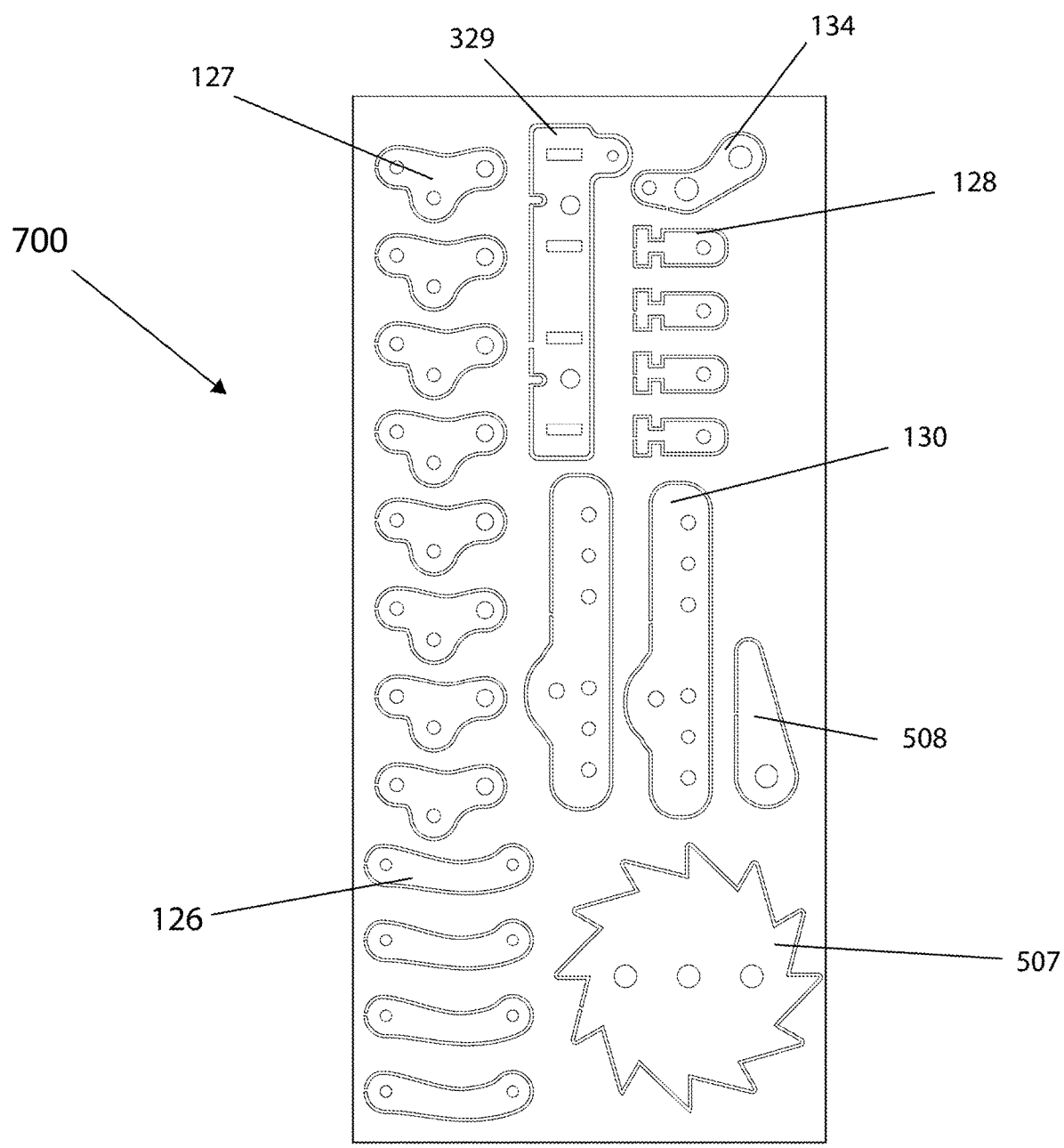
FIG. 17 depicts a plan view of exemplary force transfer elements comprising 2D shapes that are cut into and removable from a metal plate.

The metallic components of prosthetic hand apparatus 100 may be positioned to transfer forces between the polymeric components when prosthetic hand apparatus 100 is actuated to grasp an object positioned between the digits. As shown in FIGS. 1-10, the metallic components may have simpler 2D shapes that are easy to manufacture with a rapid manufacturing method, such as laser cutting with a laser cutting machine or waterjet cutting with a CNC router. Like the 3D printer, the laser cutting machine or CNC router may cut the metallic material from a metallic base material responsive to 2D cutting data. Similar to as shown in FIG. 17, any (or all) of the 2D shapes of the metallic components may be cut from a single sheet 700 of the metallic base material, such as a metal plate made of stainless steel, titanium, an alloy thereof, or any other type of material with like structural characteristics.

The engagement elements may comprise any combination of one or more bolt(s), cable(s), nut(s), pin(s), rod(s), screw(s), spring(s) and/or like mechanical elements, including the examples described herein. Some of these elements may be standardized for prosthetic hand apparatus 100, meaning that they are not made responsive to 2D or 3D data like the prosthetic and metallic components described above. In this way, prosthetic hand apparatus 100 may be economically manufactured with tremendous flexibility, allowing it to have sizing and appearance characteristics that are customizable according to the needs of each human subject.

When manufactured and assembled as described herein, prosthetic hand apparatus 100 may be stronger and more durable that it otherwise could be due to enhanced structural characteristics (e.g., strengths) of the metallic materials relative to the polymeric materials. As shown in FIGS. 1-10 and described further below, the polymeric components may be located in areas of prosthetic hand apparatus 100 where internal stresses are low when grasping an object, and the metallic components may be located in areas of prosthetic hand apparatus 100 where the internal stresses are high when grasping the object. Because the metallic components are handling most of the internal stresses, the polymeric components may be smaller and/or lighter so that prosthetic hand apparatus 100 may have both an increased strength and a reduced overall weight relative to a comparable apparatus made entirely with polymeric components.

Additional aspects of prosthetic hand apparatus 100 are now described. As shown in FIGS. 1-4, prosthetic hand apparatus 100 may comprise a base 101, a hand body 102, digits 103, a slider frame 104, and force transfer elements 105. Elements of prosthetic hand apparatus 100 may be made of different materials. In the examples now described, base 101, hand body 102, digits 103, and slider frame 104 may comprise or consist essentially of a polymeric material and thus be polymeric components; and force transfer elements 105 may comprise or consist essentially of a metallic material and thus be metallic components.

Each of base 101 and body 102 may comprise a structure with a complex 3D geometry made from a first or polymeric material utilizing an additive manufacturing method, making them polymeric components of prosthetic hand apparatus 100. As shown in FIGS. 1-4, base 101 may comprise a distal and a proximal end. The distal end of base 101 may be fixedly engageable with hand body 102. The proximal end of base 101 may comprise a ball structure that is removably engageable with a wrist structure similar to that described in U.S. patent application Ser. No. 15/194,460 to Dechev et al. (hereinafter "the '460 application"), the entirety of which is hereby incorporated by reference into this application. Various holes may extend through a central portion of base 101. As shown in FIGS. 1-4, hand body 102 may comprise cover securing elements 106, finger digit attachment portions 107, an interior cavity 108, passages 109, a thumb pivot 110, and a thumb recess 111. Cover securing elements 106 may comprise holes extending into a palmar face of hand body 102 along a palmar-dorsal axis. Finger digit attachment portions 107 may be located on a distal end of hand body 102 and comprise opposing walls with holes extending therethrough along a medial-lateral axis.

Figure 3:
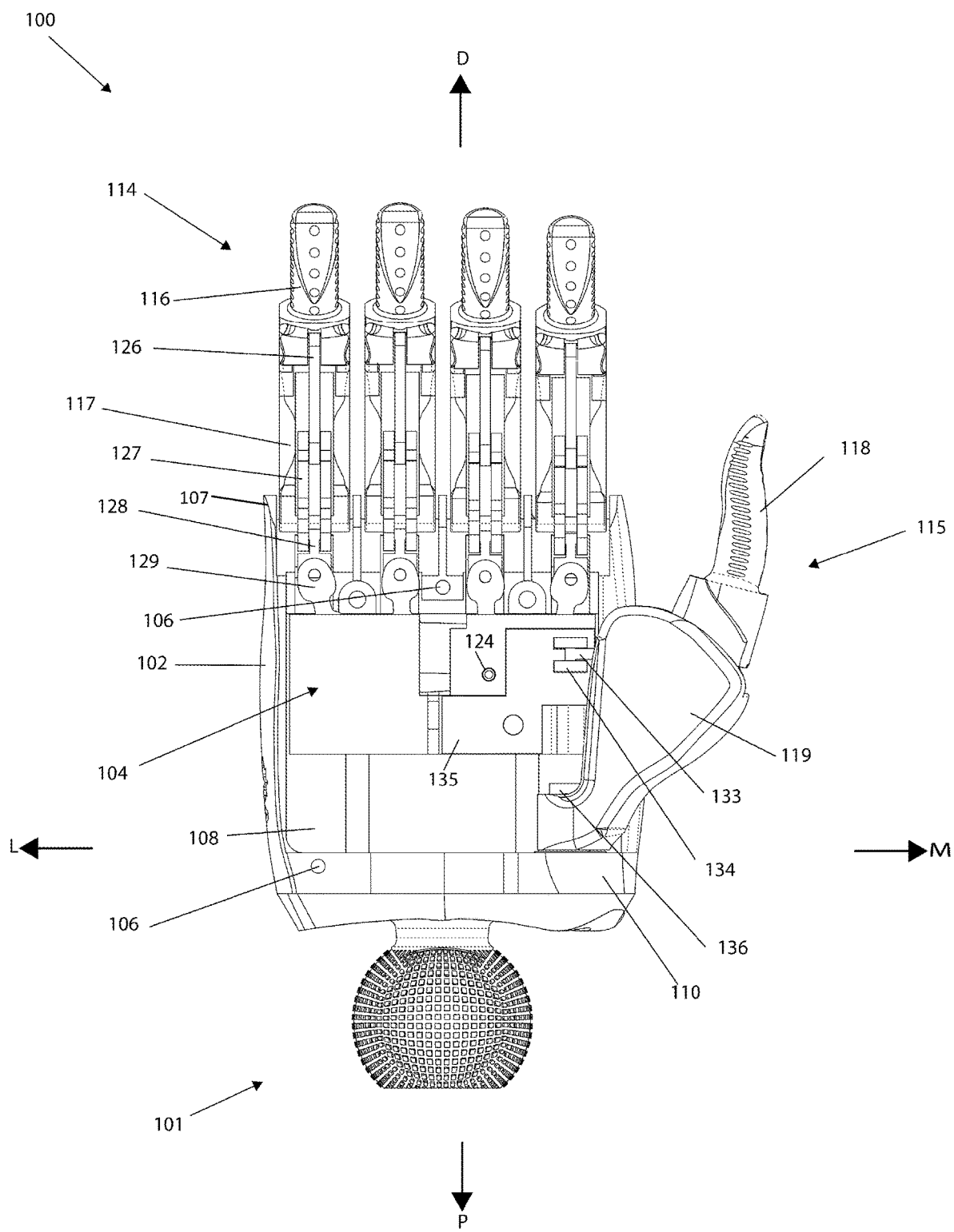
FIG. 3 depicts a palm facing view of the FIG. 1 prosthetic hand with a portion removed to show exemplary force transfer elements of the FIG. 1 prosthetic hand apparatus.
Figure 4:
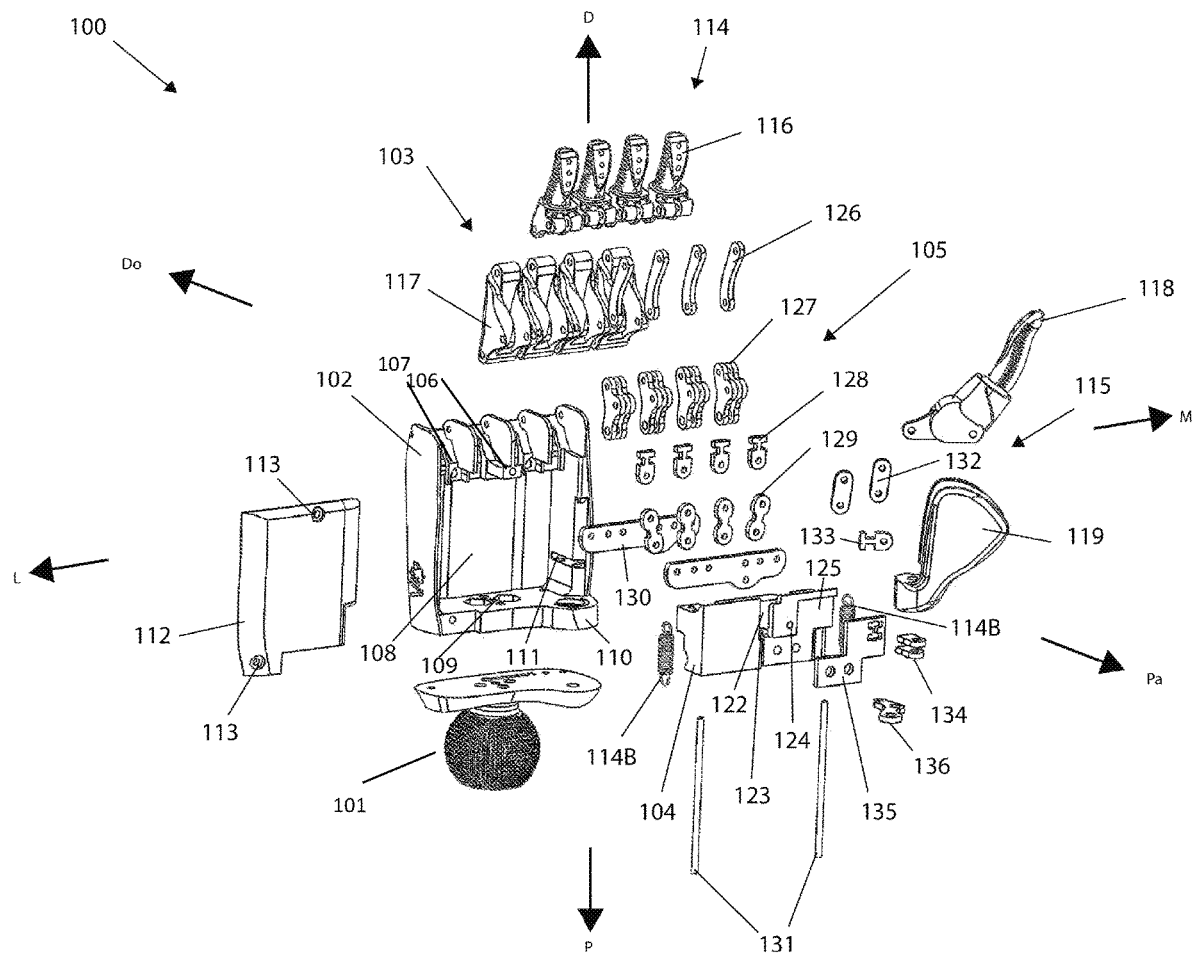
FIG. 4 depicts an exploded view of the FIG. 1 prosthetic hand apparatus.

Interior cavity 108 may comprise interior surfaces of hand body 102 that define a movement path for a slider frame 104. As shown in FIGS. 3 and 4, the interior surfaces of interior cavity 108 may comprise a medial wall, a lateral wall, and a dorsal wall that extend along a proximal-distal axis and are slidably engageable with exterior surfaces of slider frame 104, allowing it to be slid along the proximal-distal axis. As shown in FIG. 3, the palmar side of interior cavity 108 may be open. A proximal surface of finger digit attachment portions 107 may define a distal wall of interior cavity 108. A pair of rod holes may extend partially into the distal wall of interior cavity 108 along the proximal-distal axis so that they align with the pair of holes extending through the proximal wall of interior cavity 108. As shown in FIG. 4, one of finger digit attachment portions 107 may project outwardly from hand body 102 in a palmar direction to define an interlocking portion and a hole of cover securing elements 106 may extending into a palmar face of the interlocking portion.

Passages 109 may comprise a plurality of holes extending into interior cavity 108 through a proximal portion of hand body 102 along the proximal-distal axis. As shown in FIGS. 3 and 4, one hole of passages 109 may guide an actuator (e.g., a cable or rod) into interior cavity 108 and slider frame 104 through the proximal portion of hand body 102 and the central portion of base 101. Other holes of passages 109 may guide rods 131 into interior cavity 108, through corresponding holes extending through slider frame 104, and into distal portions of hand body 102. Thumb pivot 110 may comprise a rotational surface extending outwardly from proximal-medial portion of hand body 102 and a hole extending through the rotational surface along the proximal-distal axis. Thumb recess 111 may comprise an open channel extending into the medial wall of interior cavity 108 and the palmar face of hand body 102 along the palmar-dorsal axis.

Digits 103 may be movable with force transfer elements 105 between an open position (e.g., FIG. 1) and a closed position (e.g., FIG. 2) when prosthetic hand apparatus 100 is actuated by application of a proximally directed force to one of force transfer elements 105. As shown in FIGS. 1-4, digits 103 may comprise finger digits 114 and a thumb digit 115. Finger digits 114 may comprise digits of different shapes and sizes, including four different digits, one for the respective pointer, middle, index, and pinky fingers. As shown in FIGS. 1-4, each finger digit 114 may comprise a first finger link 116 and a second finger link 117, both of which may comprise a structure with a complex 3D geometry made from a polymeric material utilizing an additive manufacturing method, making them polymeric components.

First finger link 116 and second finger link 117 may resemble a human finger and appear to operate similarly. Aspects of first finger link 116 may be functionally similar to the distal and middle phalanx of a human finger. First finger link 116 may comprise a distal end, a palmar portion, and a proximal end. The distal end or tip of first finger link 116 may comprise a fingernail and a grip surface. As shown in FIG. 4, the distal end may comprise a tip region with an exposed cast surface and geometrical features extending outwardly from and/or inwardly through the exposed cast surface to define an increased surface area that is adherable with a flowable material to attach and retain a molded tip on the tip region when the flowable material is cast around the geometrical features, similar to that disclosed in the '460 application.

As shown in FIG. 4, the palmar portion and the proximal end of first finger link 116 may be spaced apart from one another in a linear formation and comprise holes extending therethrough. The palmar portion and the proximal end of first finger link 116 may comprise opposing walls and their holes may extend through their respective opposing walls. Aspects of second finger link 117 may be functionally similar to the proximal phalanx of a human finger. As shown in FIG. 4, second finger link 117 may comprise a distal end, a palmar portion, and a proximal end. The distal end, palmar portion, and proximal end of second finger link 117 may be spaced apart from one another in a triangular formation and comprise holes extending therethrough. The distal end of second finger link 117 may be receivable between the opposing walls of the proximal end of first finger link 116. The palmar portion of second finger link 117 may comprise opposing walls and its holes may extend through the opposing walls. The proximal end may of second finger link 117 be receivable between the opposing walls of finger digit attachment portions 107.

As shown in FIGS. 1-4, thumb digit 115 may comprise a thumb body 118 and a thumb base 119, each of which may comprise a structure with a complex 3D geometry made from a polymeric material utilizing an additive manufacturing method, making them polymeric components. Aspects of thumb body 118 may be similar to the distal and proximal phalanx of the human thumb. As shown in FIG. 4, thumb body 118 may comprise a distal end, an interior portion, and a proximal end. The distal end or tip of thumb body 118 may comprise a fingernail and a grip surface. As shown in FIG. 4, the distal end of thumb body 118 may comprise a tip region with an exposed cast surface like that described above with reference to the '460 application. The interior portion and proximal end of thumb body 118 may be spaced apart from one another in a linear formation and comprise holes extending therethrough. The interior portion may have an increased width relative to the proximal end.

Aspects of thumb base 119 may function similar to a first metacarpal of the human thumb. As shown in FIG. 4, thumb base 119 may comprise a distal end and a proximal end. The distal end of thumb base 119 may comprise opposing walls with holes extending therethrough. The increased width of the interior portion of thumb body 118 may be located between the opposing walls of the distal end of thumb base 119. The proximal end of thumb base 119 may comprise a rotational surface with a hole extending therethrough along the proximal-distal axis.

Figure 7:
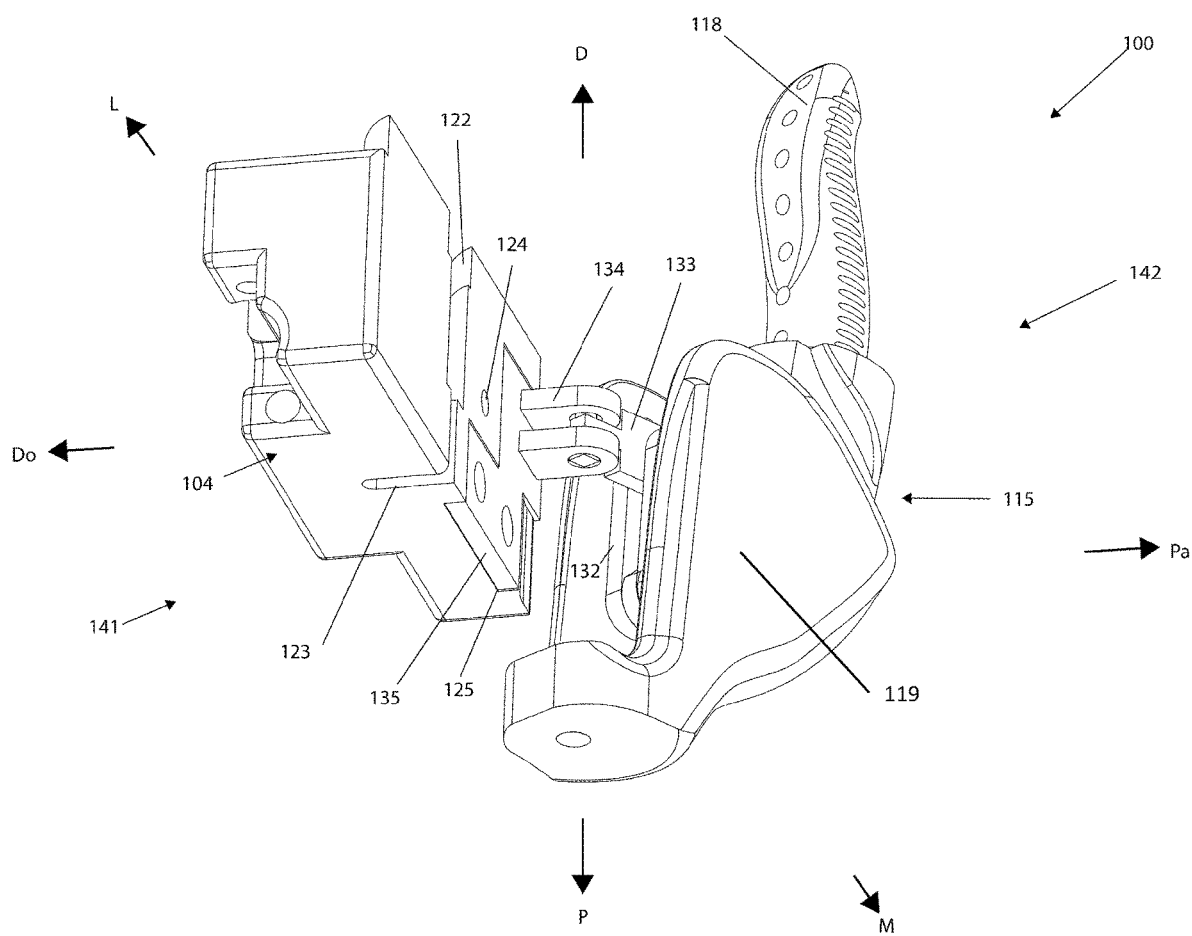
FIG. 7 depicts a perspective view of an exemplary slider plate assembly of the FIG. 1 prosthetic hand apparatus engaged with an exemplary thumb assembly of the FIG. 1 prosthetic hand apparatus.
Figure 8:
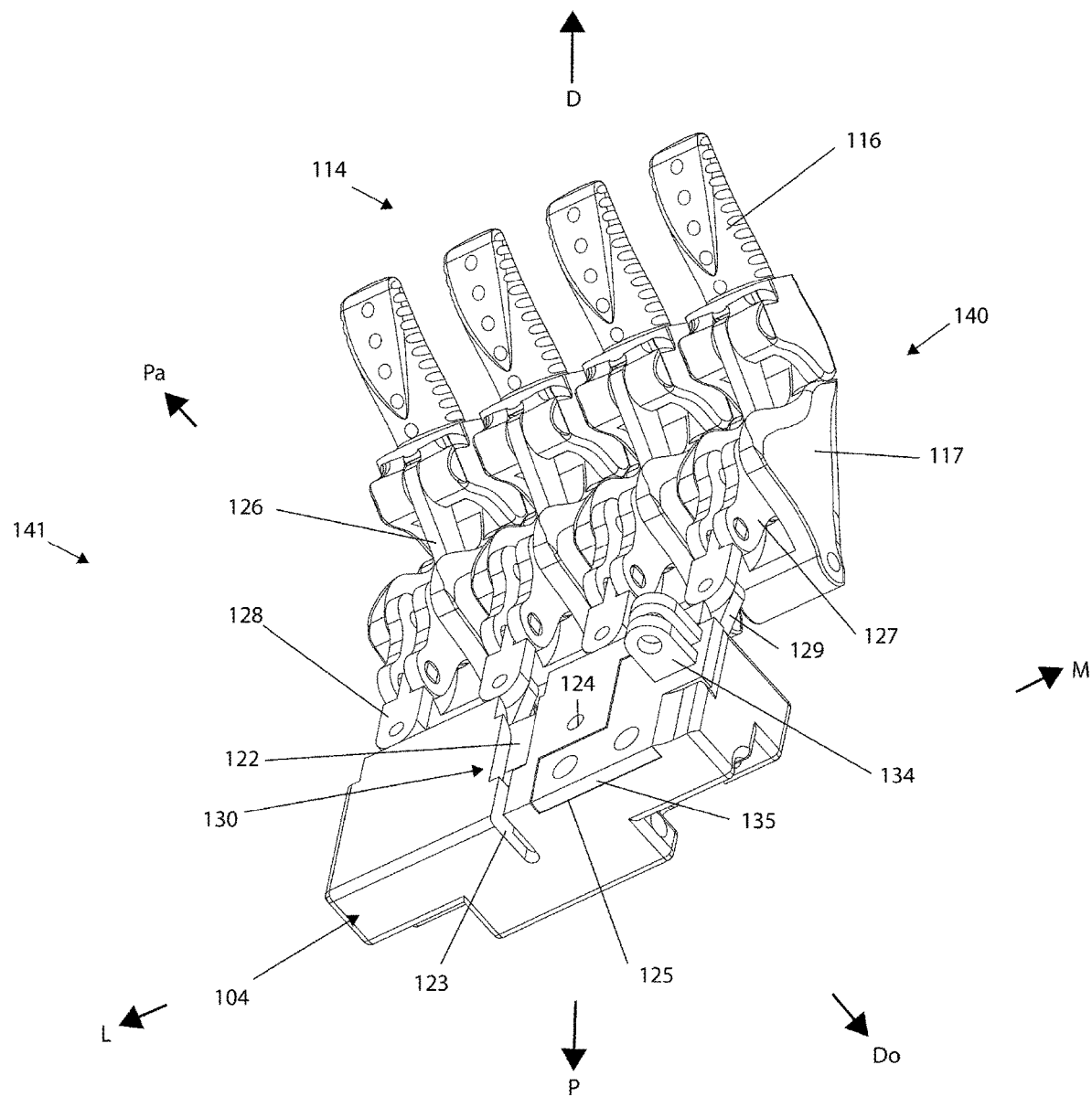
FIG. 8 depicts a perspective view of the FIG. 5 finger digit assembly engaged with the FIG. 7 slider plate assembly and thumb plate assembly.

Slider frame 104 may comprise a structure with a complex 3D geometry made from a polymeric material utilizing an additive manufacturing method, making it a polymeric component. As shown in FIGS. 4, 7, 8, and/or 10, slider frame 104 may comprise an interior cavity 122, a channel 123, a hole 124, and a thumb plate recess 125. Interior cavity 122 may be sized to contain some of force transfer elements 105. As shown in FIG. 4, interior cavity 122 may be sized to contain a rocker 130 described further below and accommodate a range of rotational motion of rocker 130 in medial and lateral directions. Dorsal portions of slider frame 104 located adjacent interior cavity 122 may comprise a pair of rod holes. Channel 123 may be formed in a palmar side of slider frame 104 to define interior surfaces that extend along the proximal-distal axis to guide the actuator towards rocker 130. Hole 124 may extend through the palmar and dorsal sides of slider frame 104 and be offset from the proximal-distal axis. As shown in FIG. 4, thumb plate recess 125 may comprise an indented portion of a medial-proximal of slider frame 104. A perimeter thumb plate recess 125 may comprise edge surfaces aligned with proximal-distal and medial-lateral axes. A proximal portion of plate recess 125 may comprise holes extending therethrough.

Figure 2:
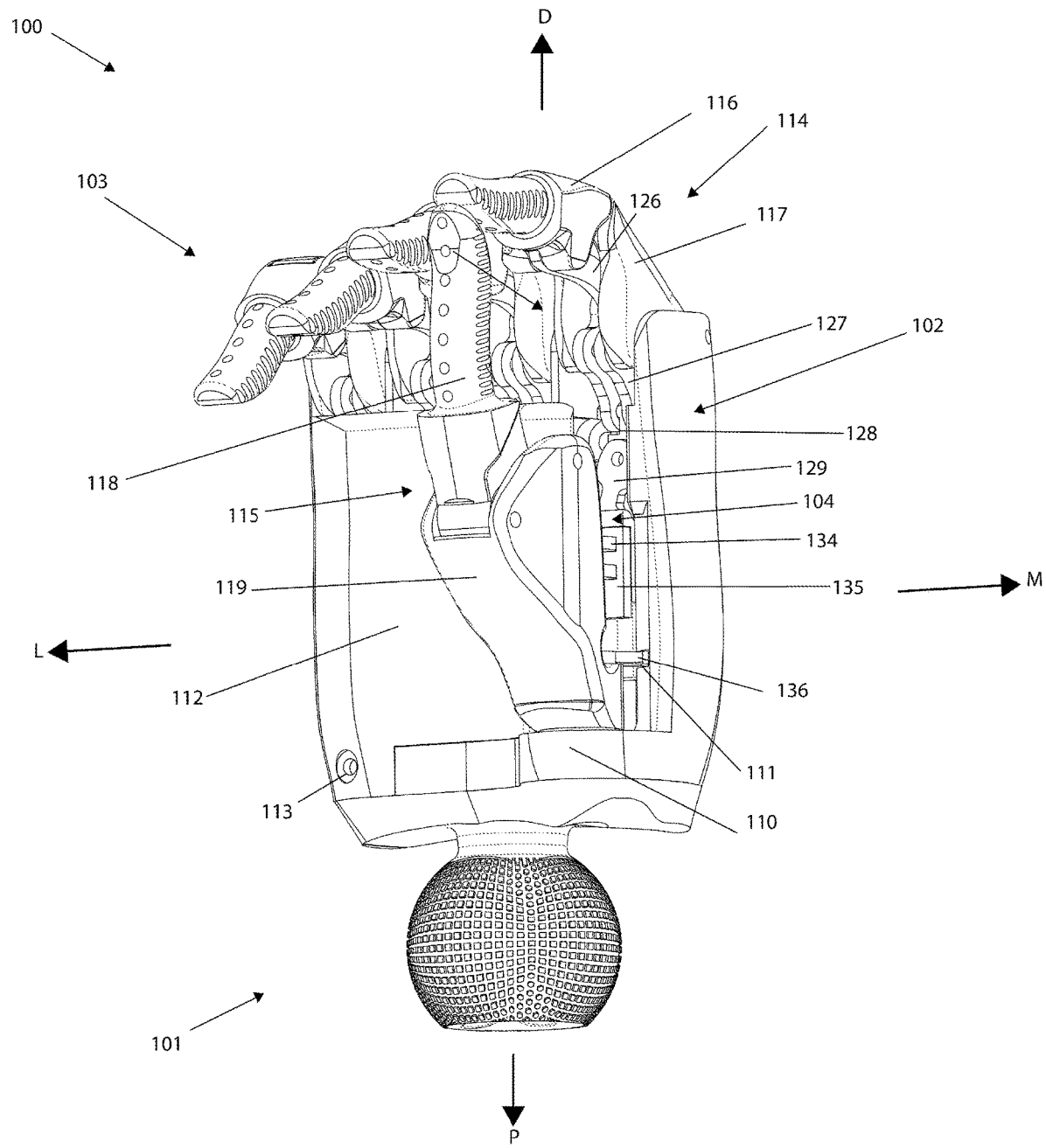
FIG. 2 depicts a perspective view of the FIG. 1 prosthetic hand apparatus.

The polymeric components of prosthetic hand apparatus 100 also may comprise a cover 112 operable to enclose interior cavity 108. As shown in FIGS. 1 and 2, cover 112 may comprise a structure defining cover securing elements 113 and a generally planar portion. Cover securing elements 113 may comprise holes extending through the generally planar portion along the palmar-dorsal axis.

Force transfer elements 105 may comprise metallic components operable to transfer forces between the prosthetic components of hand body 102, digits 103, and slider frame 104 when prosthetic hand apparatus 100 is actuated by application of a proximally directed force to one of force transfer elements 105. As shown in FIG. 4, force transfer elements 105 may comprise operational linkages for finger digits 114, rocker 130, guide elements for slider frame 104, and an operational linkage for thumb digit 115. The metallic components of force transfer elements 105 may be comprise 2D shapes made from a metallic material utilizing a rapid manufacturing method, making them metallic components. As shown in FIG. 17, the 2D shapes may be cut from a single metal plate 700 with the rapid manufacturing method, such as laser cutting or waterjet cutting, so that each 2D shape has a precision cut outer perimeter with a uniform thickness (or an approximately uniform thickness, accounting for manufacturing tolerances and defects).

The operational linkages for each finger digit 114 may comprise a third finger link 126, fourth finger links 127, a grasp link 128, a rocker link 129, and rocker 130 noted above. As shown in FIG. 4, third finger link 126 may comprise a distal end and a proximal end. The 2D shape of third finger link 126 may be aligned with the palmar-dorsal axis so that the uniform thickness of its distal end may be received between the opposing walls of the palmar portion of first finger link 116. The distal end of third finger link 126 may comprise a hole extending therethrough for alignment with the holes extending through the palmar portion of first finger link 116. The proximal end of third finger link 126 may be similarly received between the distal ends of fourth finger links 127. As shown in FIG. 4, the distal end of third finger link 126 may comprise a hole extending therethrough for alignment with holes extending through the distal ends of fourth finger links 127.

As shown in FIG. 4, fourth finger links 127 may comprise an opposing pair of 2D shapes, including a lateral plate and a medial plate that are spaced apart from one another along a medial-lateral axis, each having a distal end, a palmar portion, and a proximal end. The 2D shapes of fourth finger links 127 may be aligned with a palmar-dorsal axis so that the uniform thickness of their distal ends and palmar portions may be received between the opposing walls of the palmar portion of second finger link 117. The distal ends of fourth finger links 127 may comprise holes extending therethrough for alignment with the holes extending through the proximal portion of third finger link 126. The palmar portion of fourth finger links 127 may comprise holes extending therethrough for alignment with the holes extending through the palmar portion of second finger link 117. The proximal ends of fourth finger links 127 may comprise holes extending therethrough.

Figure 5:
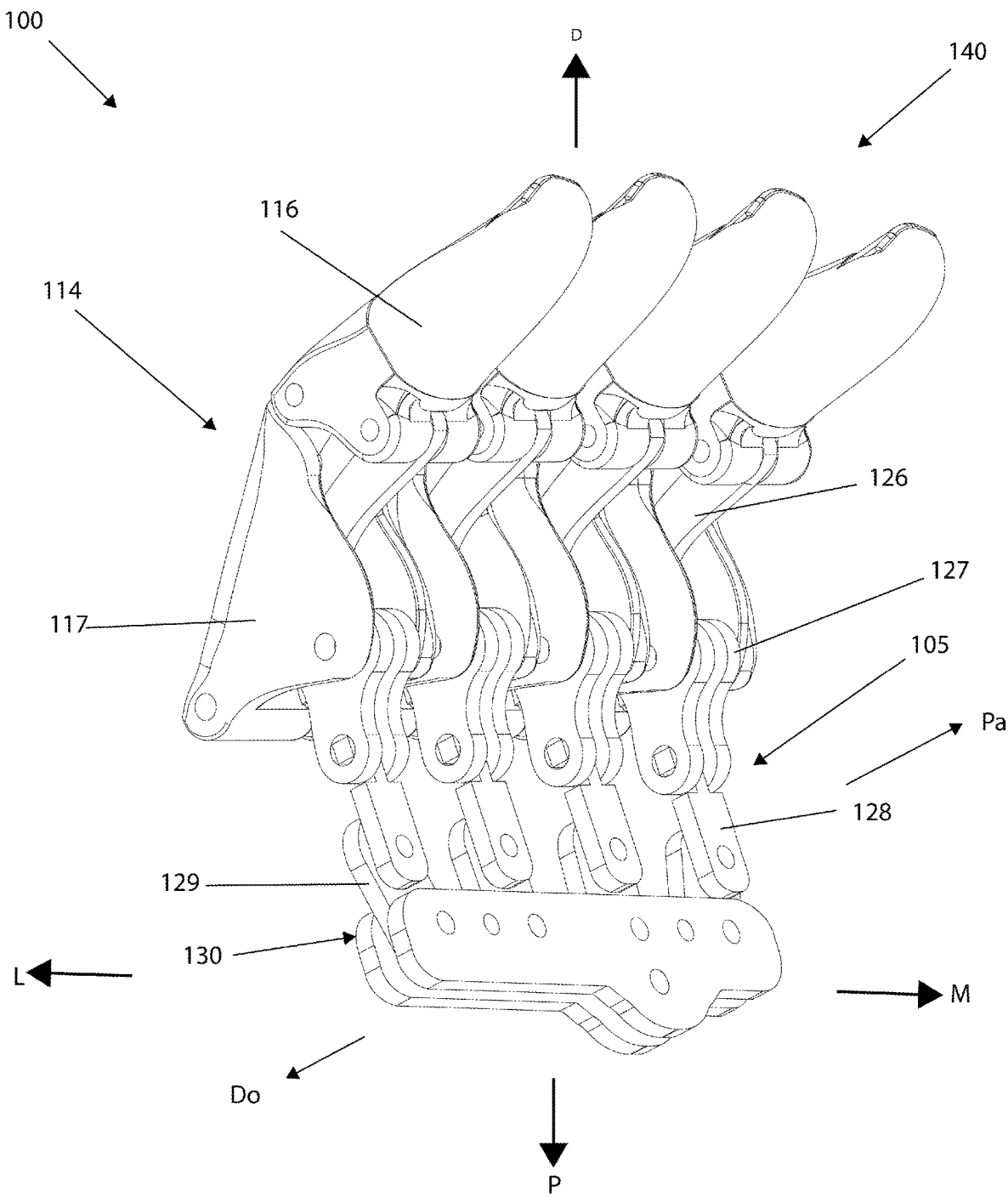
FIG. 5 depicts a perspective view of an exemplary finger digit assembly of the FIG. 1 prosthetic hand apparatus.
Figure 6:
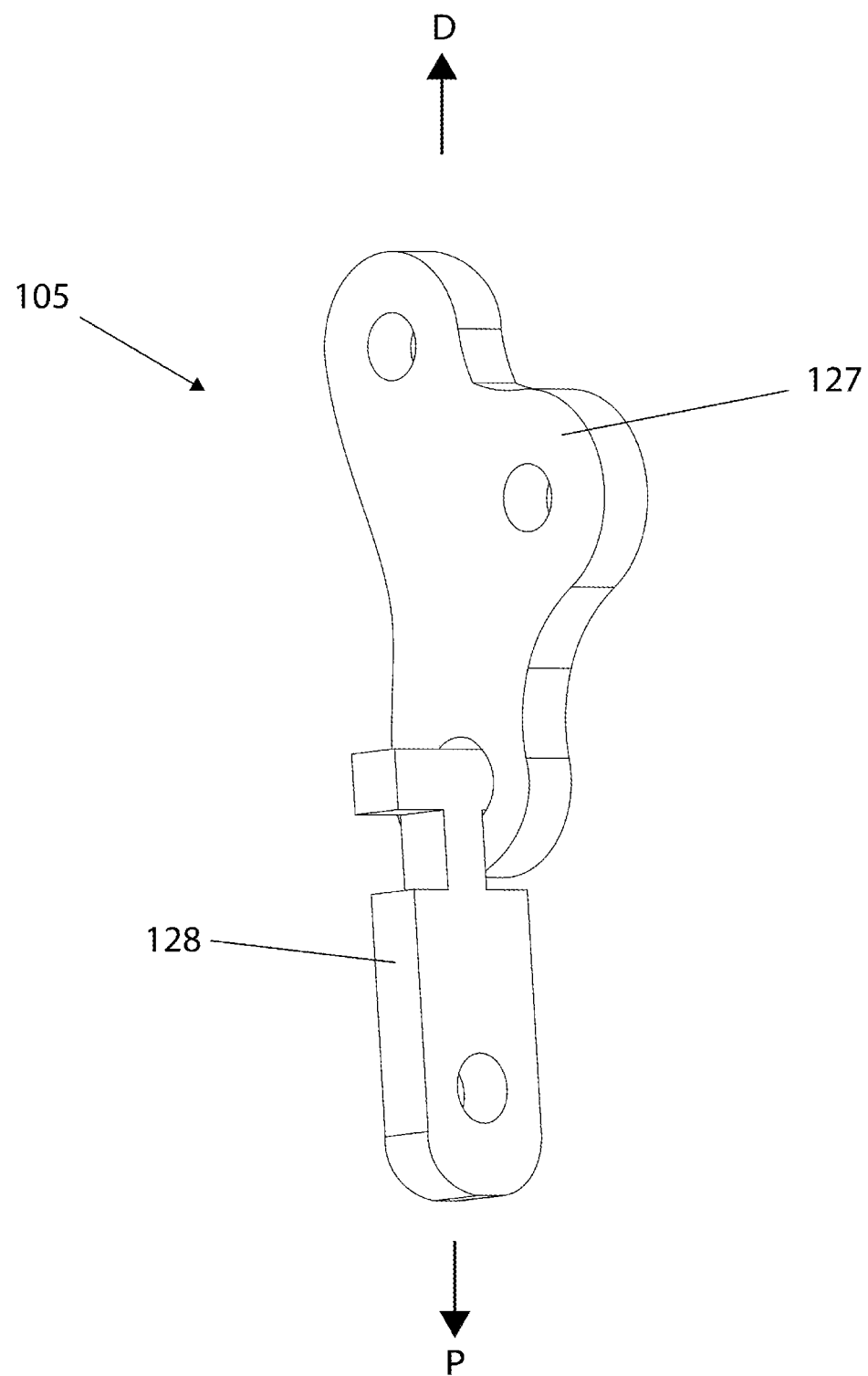
FIG. 6 depicts a perspective view of exemplary force transfer elements of the FIG. 1 prosthetic hand apparatus comprising 2D shapes that are rotationally engaged with one another.

As shown in FIG. 4, grasp link 128 may comprise a distal end and a proximal end. The 2D shape of grasp link 128 may be aligned with the medial-lateral axis and thus non-parallel with the 2D shapes of fourth finger links 127. The distal end of grasp link 128 may comprise indentions defining a narrowed neck and opposing flanges extending outwardly therefrom. As shown in FIGS. 5 and 6, the distal end of grasp link 128 may be positioned between the proximal end of fourth finger links 127 so that the opposing flanges of link 128 are received in the holes extending through the proximal ends of fourth finger links 127 and the indentions of link 128 are positioned to receive the proximal-most portions of fourth finger links 127. The proximal end of grasp link 128 may comprise holes extending therethrough.

As shown in FIG. 4, rocker link 129 may comprise a distal end and a proximal end. The 2D shape of rocker link 129 may be aligned with the medial-lateral axis and thus parallel with the 2D shape of grasp link 128. The distal and proximal ends of grasp link 128 may comprise holes extending therethrough. An interior portion of each rocker link 129 may be indented relative to its proximal and distal ends.

As shown in FIG. 4, rocker 130 may comprise a pair of opposing 2D shapes, including a palmar plate and a dorsal plate that are spaced apart from one another along the palmar-dorsal axis, each having a distal portion and a proximal portion. The distal portions of the palmar and dorsal plates of rocker 130 may comprise holes extending therethrough along the palmar-dorsal axis at spaced apart locations along the medial-lateral axis, including one hole for each rocker link 129 and a mount hole for rotationally engaging rocker 130 with slider frame 104. As shown in FIG. 4, the opposing 2D shapes of rocker 130 may be aligned with the medial-lateral axis and spaced apart along the palmar-dorsal axis so that the proximal portions of rocker links 129 may be received between the distal portions of the palmar and dorsal plates of rocker 130, allowing their respective holes to be aligned. The mount hole may be similarly aligned with hole 124 of slider frame 104. The proximal portions of the palmar and dorsal plates of rocker 130 also may comprise holes extending therethrough. An eyelet of the actuator for prosthetic hand apparatus 100 may be received between the palmar and dorsal plates of rocker 130 and comprise an eyelet hole that may be aligned with the holes extending through the proximal portions of the palmar and dorsal plates of rocker 130.

Figure 13:
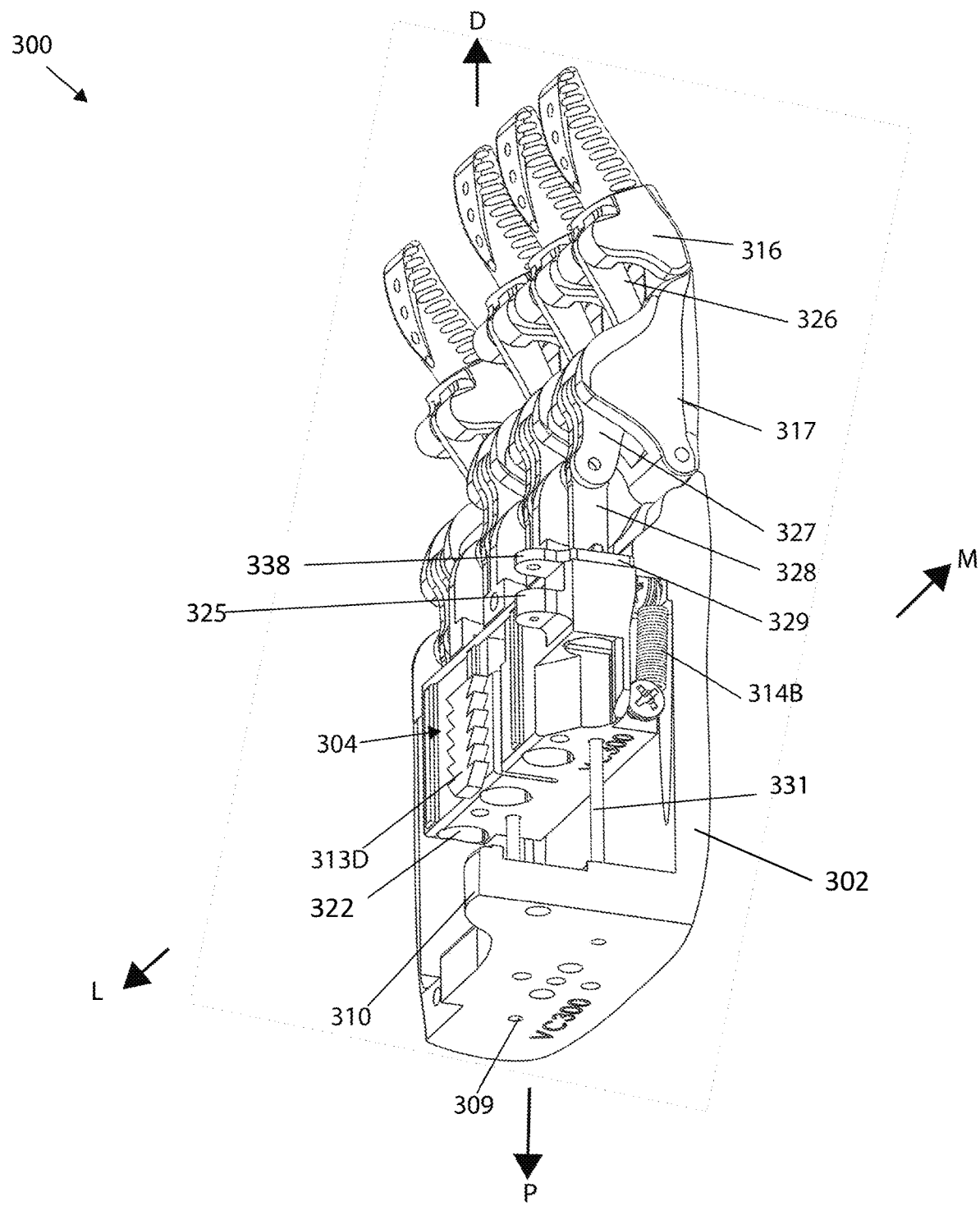
FIG. 13 depicts a side view of the FIG. 12 assemblies with a portion removed to show exemplary biasing elements.

As shown in FIG. 4, the operational linkages for finger digits 114 may comprise biasing springs 114B. Biasing spring 114B may comprise coil springs made of a metallic material, making them metallic components of prosthetic hand apparatus 100. Each biasing spring 114B may be formed by any method for making coil springs out of a metallic material, including bending and/or heating. Biasing springs 114B may be fixedly engaged with hand body 102 and slider frame 104 and operable to bias digits 103 toward the open position shown in FIG. 1. As shown in FIG. 4, a first biasing spring 114B may be mounted to lateral portions of hand body 102 and slider frame 104 and a second biasing spring 114B may be mounted to medial portions of body 102 and frame 104. Similar to as shown in FIG. 13, interior cavity 122 of slider frame 104 may comprise a lateral cut-out for the first biasing spring 114B and a medial cut-out for the second biasing spring 114B.

As shown in FIG. 4, the guide elements for slider frame 104 may comprise a pair of rods 131 inserted through the aforementioned holes extending through the proximal portion of hand body 102, the proximal and distal surfaces of its interior cavity 108, and the dorsal portions of slider frame 104 (e.g., as shown in FIG. 7). Each rod 131 may comprise a metallic component of prosthetic hand apparatus 100. For example, each rod 131 may comprise a rectangular cross-section cut from a metallic base material like the other metallic components of prosthetic hand apparatus 100 and/or a circular cross-section made by conventional means. As shown in FIG. 4, rods 131 may be contained inside the holes when base 101 is engaged with hand body 102.

The operational linkage for thumb digit 115 may be operable to convert a linear movement of slider frame 104 relative to hand body 102 into a rotational movement of thumb body 118 relative to hand body 102. As shown in FIG. 4, the operational linkage for thumb digit 115 may comprise piston plates 132, a thumb link 133, thumb connectors 134, a thumb plate 135, and a thumb pivot plate 136. Piston plates 132 may comprise an opposing pair of 2D shapes, including a lateral plate and a medial plate that are spaced apart from one another along the medial-lateral axis, each having a distal end and a proximal end. The distal and proximal ends of piston plates 132 may comprise holes extending therethrough. The 2D shapes of piston plates 132 may be aligned with thumb base 119 so that their uniform thickness may be received between the opposing walls of the distal end of thumb base 119.

Figure 9:
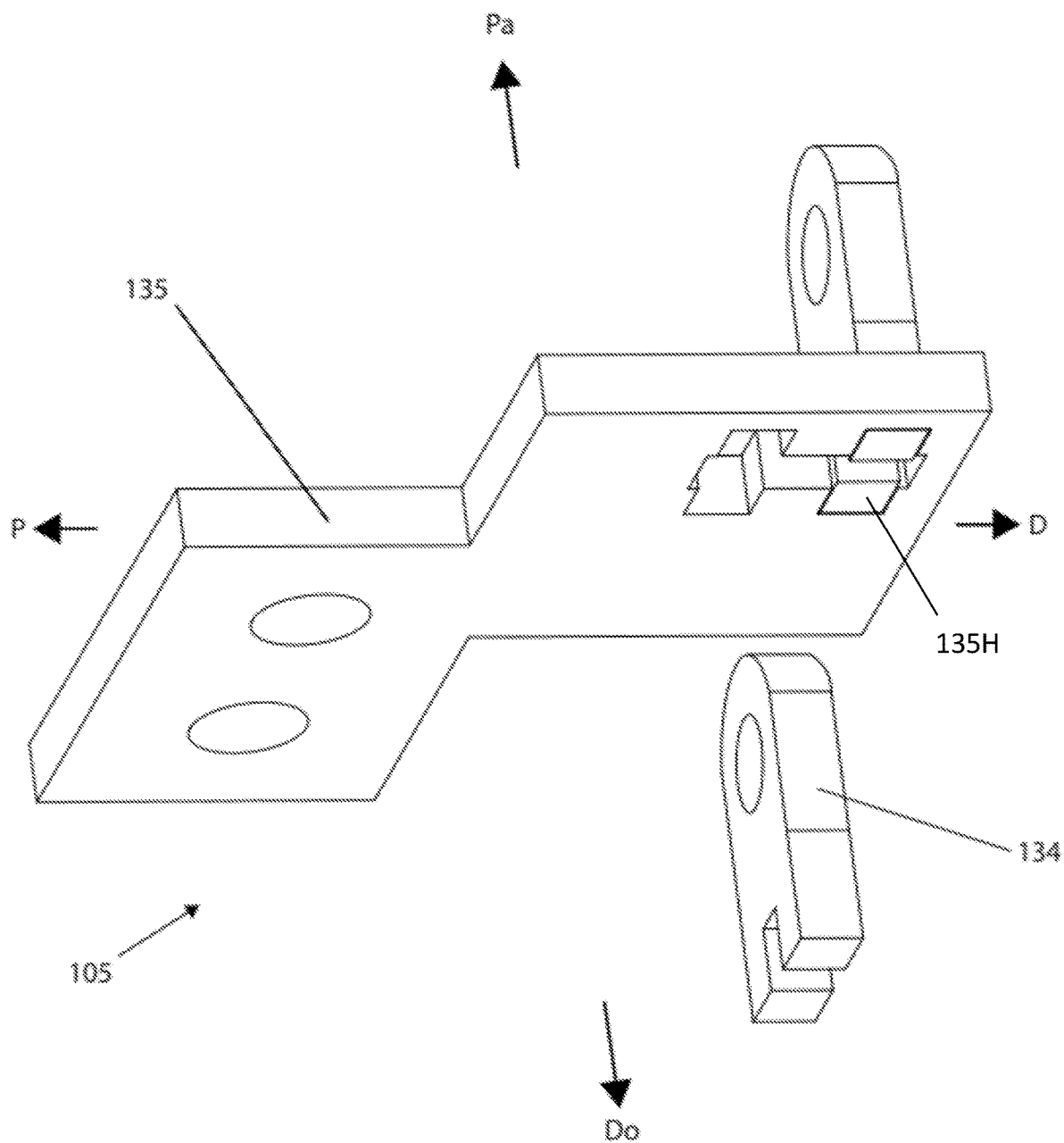
FIG. 9 depicts a perspective view of an exemplary portion of the FIG. 7 force transfer elements comprising 2D shapes that are fixedly engageable with one another to define a 3D shape.

As shown in FIG. 4, thumb link 133 may comprise a dorsal end and a palmar end. The dorsal end may comprise a hole extending therethrough. The palmar end may comprise indentions defining a narrowed neck and opposing flanges extending outwardly therefrom. Thumb connectors 134 may comprise an opposing pair of 2D shapes, each having a dorsal end and a palmar end. The dorsal and palmar ends of thumb connectors 134 may comprise rectangular cross-sections. The palmar ends may comprise holes extending therethrough. As shown in FIG. 9, the 2D shape of each thumb connector 134 may taper between a minimum width of the rectangular cross-section at its dorsal end and a maximum width of the rectangular cross-section at its palmar end. As shown in FIG. 4, the dorsal ends of each thumb connector 134 may have a solid rectangular shape that can be wedged into a hole extending through thumb plate 135. As shown in FIG. 9, the dorsal end of each thumb connectors 134 also may comprise a prong with interior surfaces defined by a channel extending through the dorsal end and exterior surfaces that slope outwardly therefrom, allowing each thumb connector 134 to be snapped into the hole of thumb plate 135.

Thumb plate 135 may be receivable in the perimeter of thumb plate recess 125 of slider frame 104. As shown in FIG. 4, edge surfaces of a perimeter of thumb plate 135 may be operable with the edge surfaces of the perimeter of thumb plate recess 125 to prevent thumb plate 135 from rotating relative to slider frame 104 when received in thumb plate recess 125. As shown in FIG. 4, thumb plate 135 may comprise a distal portion and a proximal portion. The distal portion of thumb plate 135 may comprise one or more interlocking holes 135H, each having a rectangular shape with a width approximate to the maximum widths of thumb connectors 134. As shown in FIG. 9, interlocking holes 135H may comprise a pair of first holes extending along a palmar-dorsal axis of thumb plate 135 and a second hole extending along a proximal-distal axis of thumb plate 135, giving holes 135H a barbell shape.

As shown in FIGS. 4 and 9, the rectangular cross-sections of the dorsal ends of thumb connectors 134 may be inserted through the rectangular shape of the interlocking holes of thumb plate 135 in a palmar direction until the palmar ends of thumb connectors 134 are wedged into the interlocking holes. The proximal portion of thumb plate 135 may comprise one or more attachment holes that may be aligned with the one or more attachment holes of slider frame 104 when thumb plate 135 is received in thumb plate recess 125.

Thumb pivot plate 136 may prevent thumb digit 115 from pulling away from hand body 102. A shown in FIG. 4, thumb pivot plate 136 may comprise a dorsal end and a palmar end. The dorsal end of thumb pivot plate 136 may be receivable in thumb recess 111 and comprise holes extending therethrough along the proximal-distal axis. The palmar end of thumb pivot plate 136 may comprise a 2D shape that is positionable on the rotational surface of the proximal end of thumb base 119 and a hole extending therethrough for alignment with the holes extending through the rotational surface of thumb pivot 110 and the rotational surface of thumb base 119.

Figure 19:
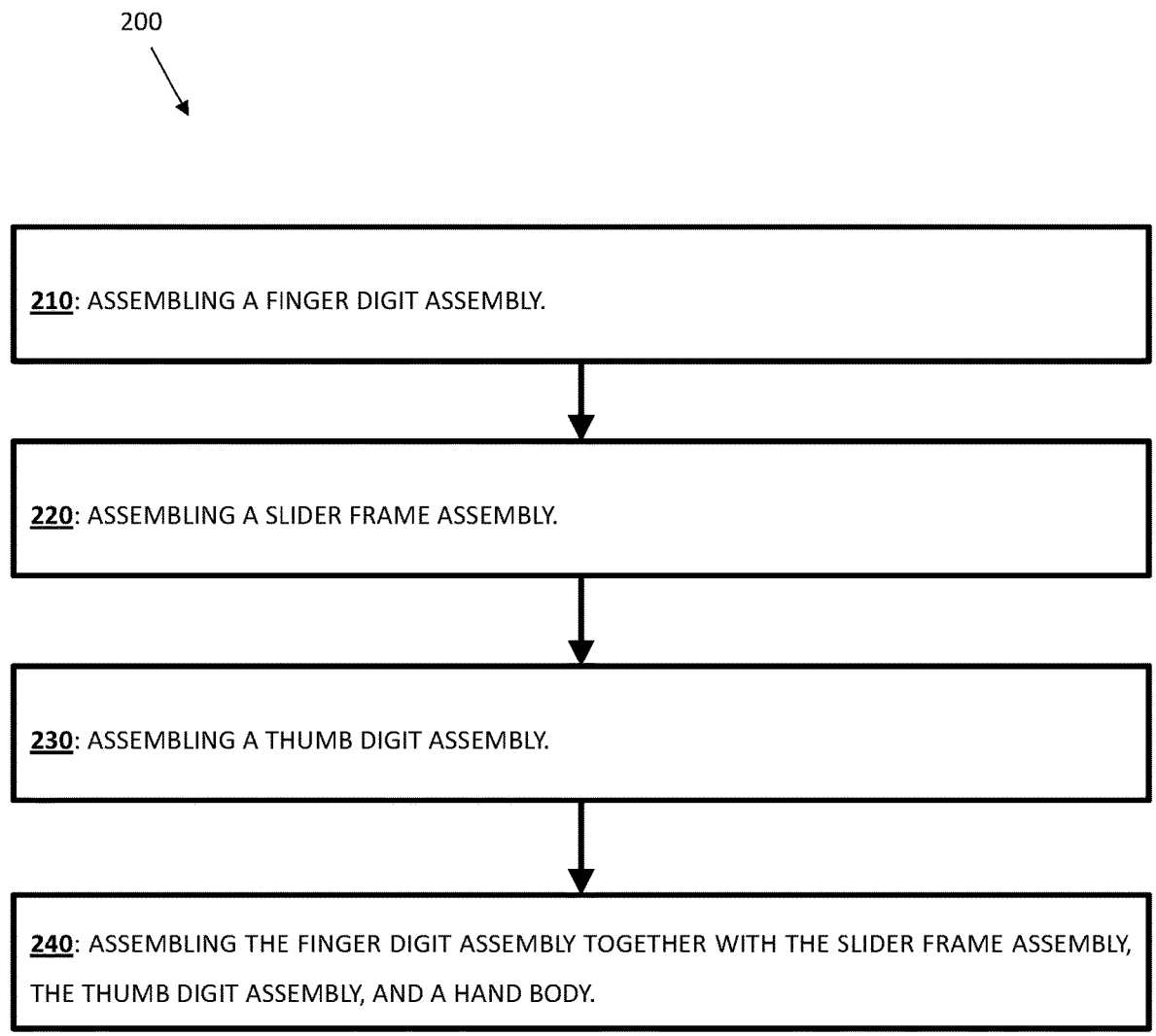
FIG. 19 depicts an exemplary assembly method.

Methods of assembling prosthetic hand apparatus 100 are now described with reference to an assembly method 200. As shown in FIG. 19, assembly method 200 may comprise: (i) assembling a finger digit assembly 140 (a step 210); (ii) assembling a slider frame assembly 141 (a step 220); (iii) assembling a thumb digit assembly 142 (a step 230); and (iv) assembling finger digit assembly 140 together with slider frame assembly 141, thumb digit assembly 142, and hand body 102 (a step 240). Each of steps 210-240 may comprise intermediate steps in keeping with the structural and functional descriptions of prosthetic apparatus 100 set forth in this disclosure.

An example of finger digit assembly 140 is shown in FIG. 5. In keeping therewith, step 210 may comprise assembling finger digit assembly 140 by rotatably engaging first finger links 116, second finger links 117, third finger links 126, fourth finger links 127, grasp links 128, rocker links 129, and rocker 130. Each rotational engagement may function similar to a pinned connection, in which a metal pin or equivalent rotational surface is inserted through the various holes described above and secured to the various structures associated therewith. For example, step 210 may comprise: (a) receiving the distal ends of third finger links 126 between the opposing walls of the palmar portions of first finger links 116, aligning their respective holes, inserting pins through the holes, and securing the pins thereto (a step 211); (b) receiving the distal ends of second finger links 117 between the opposing walls of the proximal ends of first finger links 116, aligning their respective holes, inserting pins through the holes, and securing the pins thereto (a step 212); (c) receiving the proximal ends of third finger links 126 between the distal ends of fourth finger links 127, aligning their respective holes, inserting pins through the holes, and securing the pins thereto (a step 213); (d) receiving the palmar portions of fourth finger links 127 between the palmar portions of second finger links 117, aligning their respective holes, inserting pins through the holes, and securing the pins thereto (a step 214); (e) receiving the opposing flanges of the distal ends of grasp links 128 in the holes of the proximal ends of fourth finger links 127, as shown in FIG. 6 (a step 215); (f) aligning the holes of the proximal portions of grasp links 128 with the holes of the distal ends of rocker links 129, inserting pins through the holes, and securing the pins thereto (a step 216); and (g) receiving the proximal ends of rocker links 129 between the palmar and dorsal plates of rocker 130, aligning their respective holes, inserting pins through the holes, and securing the pins thereto (a step 217).

Figure 10:
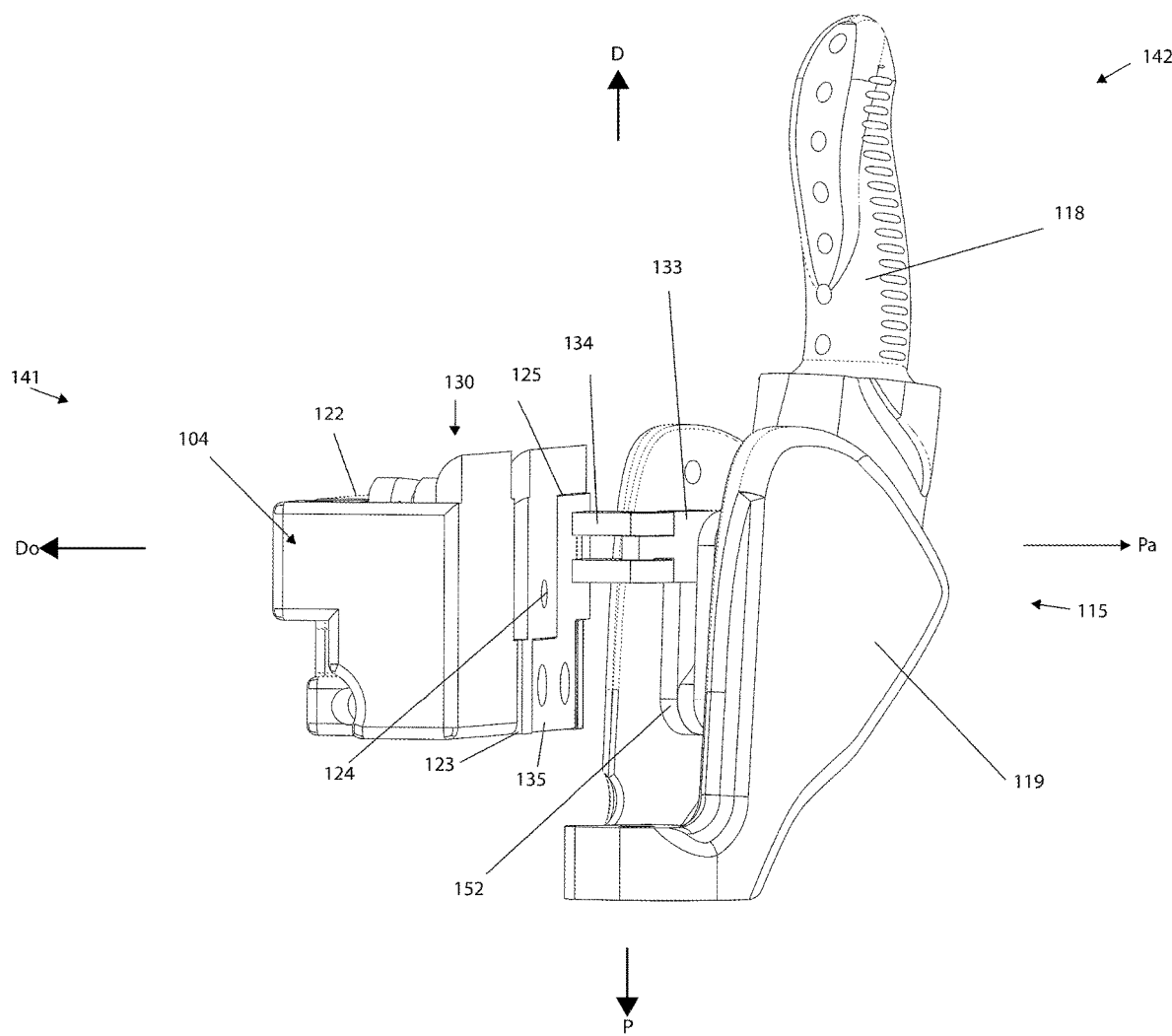
FIG. 10 depicts an alternate perspective view of the FIG. 7 assemblies.

An example of slider frame assembly 141 is shown in FIGS. 7, 8, and 10. In keeping therewith, step 220 may comprise assembling slider frame assembly 141 by fixedly engaging slider frame 104 with thumb link 133, thumb connectors 134, and thumb plate 135. For example, step 220 may comprise: (a) receiving the opposing flanges of the dorsal ends of thumb link 133 in the holes of the palmar ends of thumb connectors 134 (e.g., FIG. 10) (a step 221); (b) inserting the palmar ends of thumb connectors 134 through the interlocking holes of thumb plate 135 and moving thumb connectors 134 and thumb link 133 through the one or more interlocking holes 135H, meaning through the first pair of holes and the second hole respectively, until the dorsal ends of thumb connectors 134 are wedged and/or snapped into the pair of first holes (e.g., FIG. 9); (a step 222); (c) inserting the perimeter of thumb plate 135 into the perimeter of slider plate recess 125 and aligning the holes of slider frame 104 with the holes of thumb plate 135 (a step 223); and (d) securing thumb plate 135 in slider plate recess 125 by inserting screws through the holes of slider frame 104 and thumb plate 135.

An example of thumb digit assembly 142 is shown in FIG. 7. As shown, step 230 may comprise assembling thumb digit assembly 142 by rotatably engaging thumb body 118, thumb base 119, piston plates 132, thumb link 133, thumb connectors 134, and thumb plate 135. For example, step 230 may comprise: (a) receiving the proximal end of thumb body 118 between the distal ends of piston plates 132, aligning their respective holes, inserting pins through the holes, and securing the pins thereto (a step 231); and (b) receiving the interior portion of thumb body 118 between the opposing walls of the distal end of thumb base 119, aligning their respective holes, inserting pins through the holes, and securing the pins thereto (a step 232).

Once finger digit assembly 140, slider frame assembly 141, and thumb digit assembly 142 have been assembled, step 240 may further comprise engaging those elements to form prosthetic hand apparatus 100. For example, step 240 may comprise: (a) rotatably engaging slider frame assembly 141 and thumb digit assembly 142 by receiving the palmar end of thumb link 133 between the proximal ends of piston plates 132, aligning their respective holes, inserting pins through the holes, and securing the pins thereto, as shown in FIGS. 3, 4, 7 and 10 (a step 241); (b) rotatably engaging hand body 102 with slider frame assembly 141 and thumb digit assembly 142 by receiving the proximal ends of second finger links 117 between the opposing walls of finger digit attachment portions 107, aligning their respective holes, inserting pins through the holes, and securing the pins thereto (a step 242); (c) locating rocker 130 inside interior cavity 122 of slider frame 104, aligning the mount hole of the distal portions of the palmar and dorsal plates of rocker 130 with hole 124 of slider frame 104, inserting pins through the holes, and securing the pins thereto (a step 243); (d) rotating slider frame assembly 141 and thumb digit assembly 142 about finger digit attachment portions 107 to locate slider frame assembly 141 inside of interior cavity 108 and position the rotational surface of thumb base 119 adjacent the rotational surface of thumb pivot 110 (a step 244); (e) inserting the dorsal end of thumb pivot plate 136 into thumb recess 111 and positioning the palmar end of thumb pivot plate 136 on the rotational surface of thumb base 119 (a step 245); (f) inserting screws through hand body 102 and into the holes of the palmar end of thumb pivot plate 136 to secure it in thumb recess 111 (a step 246); (g) inserting a rod through the holes of the dorsal end of thumb pivot plate 136 and the rotational surfaces of thumb pivot 110 and thumb link 119 and securing the rod thereto (a step 247); (h) receiving rods 131 in the various holes described above and securing base 101 to hand body 102 to contain rods 131 therein (a step 248); and (i) positioning cover 112 over interior cavity 108 and inserting screws into the openings of cover securing elements 106 and 113 (a step 249).

Once prosthetic hand apparatus 100 has been assembled according to method 200 described above (or its equivalent), then it may be actuated to grasp an object with digits 103 when a proximally directed force is applied to rocker 130 with the actuator. Force transfer elements 105 may be configured for different types of grips. For example, force transfer elements 105 may be configured to perform an "adaptive grip" in which, responsive to the proximally directed force, a first portion of finger digits 114 are moved toward hand body 102 at a first rate, a second portion of digits 114 are moved toward hand body 102 at a second rate, and the first rate is faster than the second rate so that digits 103 close in more hand-like manner.

As shown in FIG. 1, finger digits 114 may comprise a pointer finger, a middle finger, a ring finger, and a pinky finger. Prosthetic hand apparatus 100 may be operable between an open position (e.g., FIG. 1), a closed position (e.g., FIG. 2), and a plurality of intermediate positions (e.g., FIG. 3). An exemplary open position of prosthetic hand apparatus 100 is shown in FIG. 1, in which finger digits 114 and thumb digit 115 are fully extended. The open position may be the default position. For example, as shown in FIG. 4, biasing springs 114B may be configured slider frame 104 distally so that digits 114 and 115 are biased open toward a fully extended state.

An exemplary closed position of prosthetic hand apparatus 100 is shown in FIGS. 2 and 4, in which finger digits 114 and thumb digit 115 are fully closed. The closed position may be realized when the proximally directed force is applied to rocker 130 by the actuator, causing slider frame 104 engaged therewith to slide proximally within interior cavity 108 by overcoming any distally directed forces applied by biasing springs 114B. As it moves, rocker 130 may distribute the proximally directed force to rocker links 129 for further distribution to grasp links 128 and fourth finger links 127, causing them to rotate third finger links 126, which may then act through first links 116, second links 117, and hand body 102 to close digits 103.

As shown in FIGS. 2 and 4, each finger digit 114 may close at different rates of speed and with different degrees of closure. The pointer finger of finger digits 114 may rotate faster and close to a greater degree than the middle, index, and pinky fingers of finger digits 114 so that the grasp surface of the pointer finger may contact the grasp surface of thumb body 118 when prosthetic hand apparatus 100 is in the closed position. The middle finger of finger digits 114 may rotate slower and close to a lesser degree than the index finger of digits 114, and the index finger may rotate slower and close to a lesser degree than pinky finger of finger digits 114, allowing prosthetic hand apparatus 100 to assume a more life-like position in the closed position.

The different rates of speed and degrees of closure may be determined by the spacing between the holes extending through the distal portions of the palmar and dorsal plates of rocker 130 and the holes extending through the proximal portions of the palmar and dorsal plates of rocker 130. As shown in FIG. 4, the proximally directed force may be applied to the proximal holes of rocker 130 along the proximal-distal axis and transferred to slider frame 104 via a pin extending through the mount hole of rocker 130 and hole 124 of slider frame 104. Hole 124 may be offset from the proximal-distal axis so that the proximally directed force causes rocker 130 to rotate. Each distal hole of rocker 130 and thus each rocker link 129 may be spaced apart from the proximal-distal axis along the medial-lateral axis by different distances so that different portions of the proximally directed force may be transferred to each finger digit 114. The distal hole for rocker link 129 of the point finger of finger digits 114 may be spaced apart from the proximal-distal axis by a first distance, the distal hole for rocker link 129 of the middle finger of finger digits 114 may be spaced apart from the proximal-distal axis by a second distance, and the first distance may be greater than the second distance so that the output forces transferred to the pointer finger are different from the output forces transferred to the middle finger digit, causing those fingers to close at different rates of speed and/or to a different degree. The same can be said of each different finger digit 114, each of which may be spaced apart from the proximal-distal axis by a different distance, causing them to close at different rates and degrees.

The above-described rotatable engagement between slider frame 104, rocker 130, and the actuator may thus allow the grasp of prosthetic hand apparatus 100 to adapt when grasping an object, providing prosthetic hand apparatus 100 an "adaptive grasp" like that described in the '460 application. The grasping surfaces of the pointer finger of finger digits 114 and thumb digit 115 may be utilized to grasp any object in this manner. As shown in FIGS. 2 and 4, prosthetic hand apparatus 100 may be moved toward the object in the open position until the object is located proximate to pointer finger of finger digits 114 and thumb digit 115, which may be rotated laterally as needed to locate a grasp surfaces of finger digits 114 is opposite of a grasp surface of thumb digit 115. The proximally directed force may then be applied to rocker 130 by the actuator, causing the grasp surfaces of digits 114, 115 to move toward one another until they contact the object. At this point, reaction forces applied by the object may be greater than the closing forces applied by digits 114, 115, causing forces to be redistributed back to digits 114, 115, with rocker 130 until a state of equilibrium is reached. In response to the proximally directed force, prosthetic hand apparatus 100 may thus apply an initial amount of force to grasp the object, then cause digits 114 to close fully, and then cause an additional amount of force to be applied to the object, helping to retain the object between the grasping surfaces.

Aspects of prosthetic hand apparatus 100 may be applicable to any type of terminal unit and/or related prosthetics. To provide some additional examples, aspects of exemplary prosthetic hand apparatus 300, 900 are now described. Aspects of prosthetic hand apparatus 300, 900 may be similar or identical to aspects of prosthetic hand apparatus 100, but within the 300 or 900 series of numbers. As shown in FIGS. 11-14 and 23-24, components of prosthetic apparatus 300, 900 may be similarly manufactured with low-cost manufacturing methods to help a subject (e.g., a human) with a partial limb regain some normal functions.

Like prosthetic hand apparatus 100, prosthetic apparatus 300, 900 also may comprise combinations of first components such as polymeric components, second components such as metallic components, and engagement elements operable therewith, as those terms are described above. As before, the metallic components may comprise 2D shapes for adding strength and the polymeric components may comprise 3D shapes for customizing appearance and size.

Figure 11:
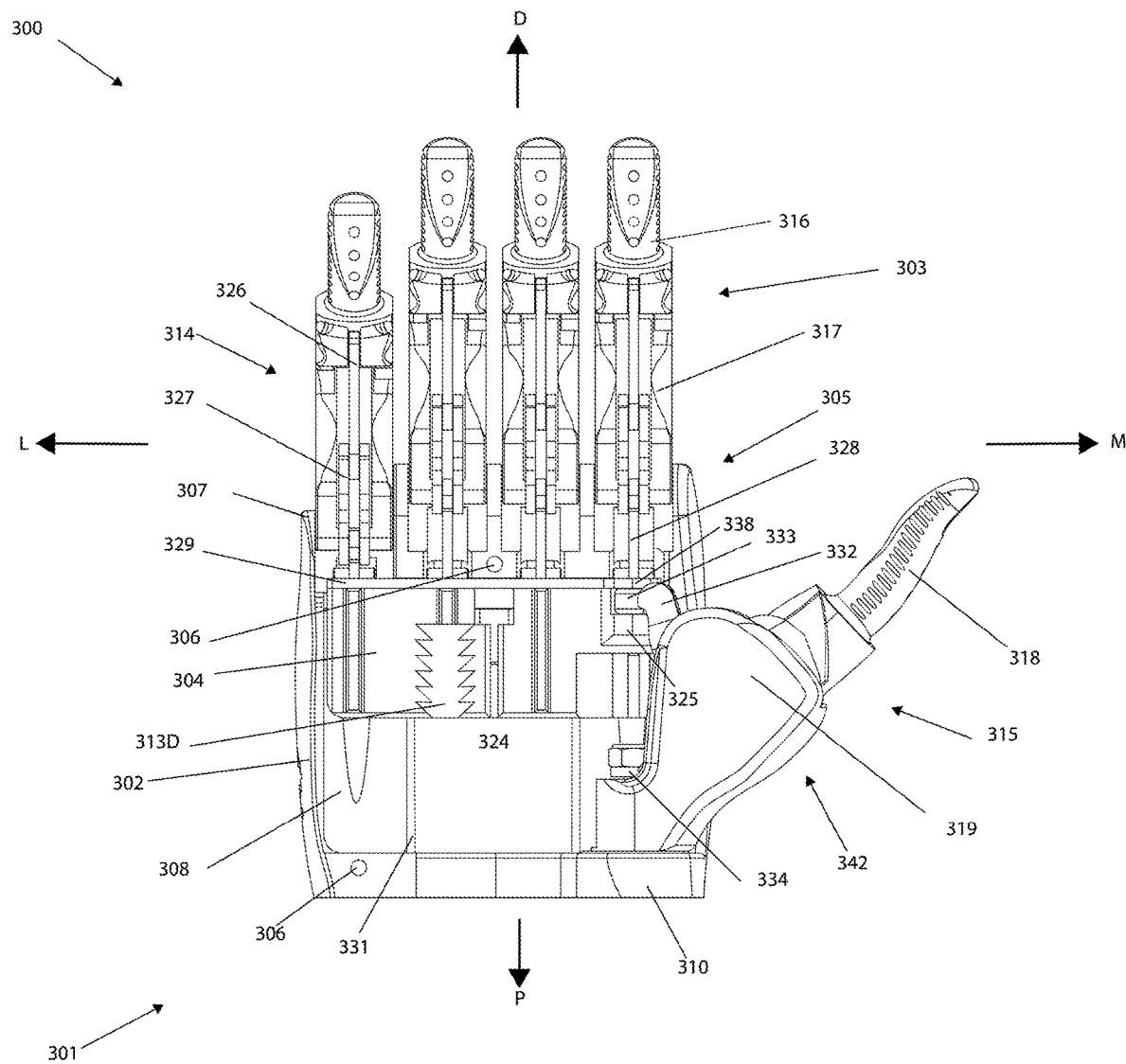
FIG. 11 depicts a palm facing view of another exemplary prosthetic hand apparatus.
Figure 12:
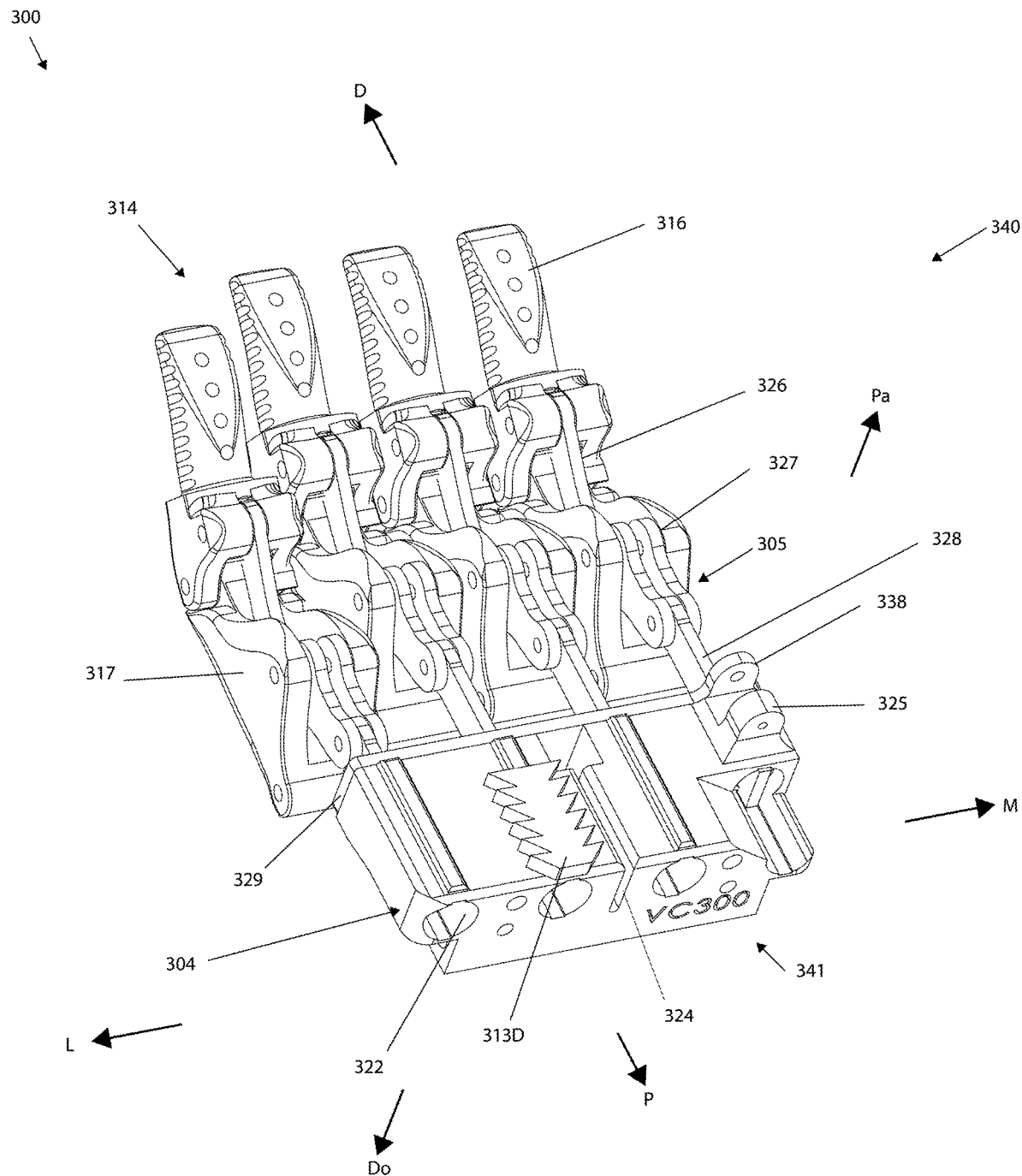
FIG. 12 depicts a perspective view of a finger digit assembly of the FIG. 11 prosthetic hand apparatus engaged with a slider plate assembly of the FIG. 11 apparatus.

For ease of description, a number of structural and functional differences are now described with continued reference to prosthetic hand apparatus 100. Any differences described in relation to prosthetic hand apparatus 300, 900 may be similarly applied to prosthetic hand apparatus 100 or any other prosthetic apparatus described herein and vice versa, each possible iteration being part of this disclosure. As shown in FIGS. 11, 12, 13 and/or 14, prosthetic hand apparatus 300 may comprise a base 301, a hand body 302, digits 303, a slider frame 304, and force transfer elements 305. Components of prosthetic hand apparatus 300 also may be made of at least two different materials. In the examples now described, as above, base 301, hand body 302, digits 303, and slide frame 304 may be manufactured (e.g., 3D printed) with a polymeric base material as "polymeric components" and some of force transfer elements 305 may be manufactured (e.g., laser or water cut) with a metallic base material as "metallic components."

Figure 14:
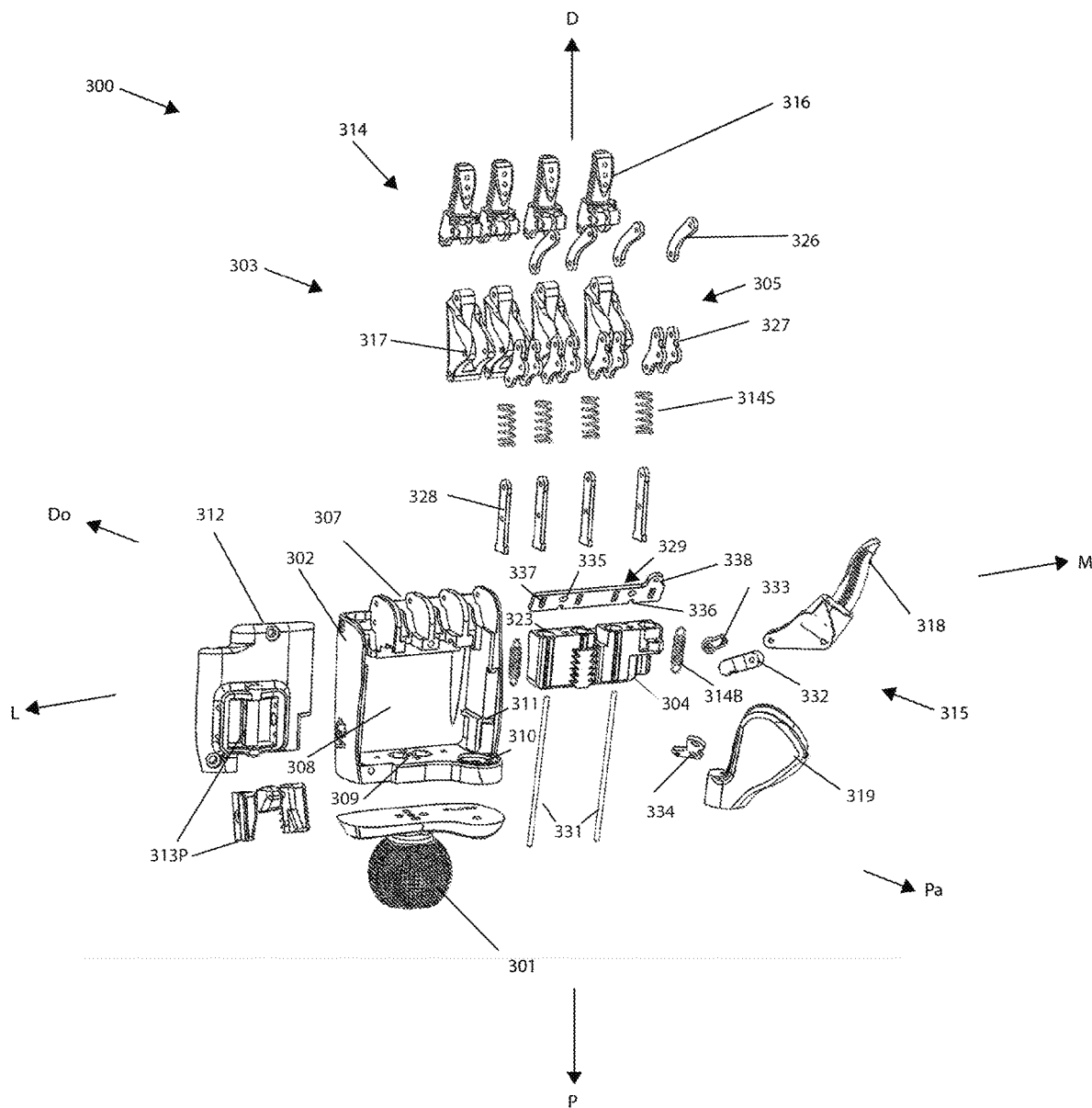
FIG. 14 depicts an exploded view of the FIG. 11 prosthetic hand apparatus.

Each of base 301 (e.g., FIG. 14) and body 302 may comprise a structure with a complex 3D geometry made from a polymeric material utilizing an additive manufacturing method, making them polymeric components of prosthetic hand apparatus 300. Base 301 may be similar to base 101 of prosthetic hand apparatus 100. As shown in FIGS. 11-14, hand body 302 may comprise cover securing elements 306, finger digit attachment portions 307, an interior cavity 308, passages 309, a thumb pivot 310, and a thumb recess 311, each of which may be similar to counterpart elements of prosthetic hand apparatus 100 described above. Passages 309 may comprise a plurality of holes extending into interior cavity 308 through a proximal portion of hand body 302 along the proximal-distal axis. As shown in FIGS. 11, 13 and 14, one hole of passages 309 may guide an actuator (e.g., a cable or rod) into interior cavity 308 and slider frame 304 through the proximal portion of hand body 302 and the central portion of base 301. Other holes of passages 309 may guide rods 331 into interior cavity 308, through corresponding holes extending through slider frame 304, and into distal portions of hand body 302.

Digits 303 may be movable with force transfer elements 305 between an open position (e.g., FIG. 11) and a closed position (e.g., similar to FIG. 2) when prosthetic hand apparatus 300 is actuated by application of a proximally directed force to one of force transfer elements 105. As shown in FIGS. 11-14, digits 303 may comprise finger digits 314 and a thumb digit 315. Finger digits 314 may comprise digits of different shapes and sizes, including four different digits, one for the respective pointer, middle, index, and pinky fingers. As shown in FIG. 12, each finger digit 314 may comprise a first finger link 316 and a second finger link 317 that are similar to counterpart elements of prosthetic hand apparatus 100 described above. Each link 316 and 317 may similarly comprise a structure with a complex 3D geometry made from a polymeric material utilizing an additive manufacturing method, making them polymeric components. A distal end or tip of first finger link 116 may similarly comprise a tip region with an exposed cast surface like that described above with reference to the distal end or tip of first finger link 116 of apparatus 100.

As shown in FIGS. 11 and 14, thumb digit 315 may comprise a thumb body 318 and a thumb base 319, each of which may be similar to counterpart elements of prosthetic hand apparatus 100 described above. Thumb body 318 and thumb base 319 may similarly comprise structures with complex 3D geometries made from a polymeric material utilizing an additive manufacturing method, making them polymeric components similar to thumb body 118 and thumb base 119 described above.

In contrast to above, an operational linkage for thumb digit 315 may comprise polymeric components such as a thumb link 332 and a thumb connector 333. As shown in FIG. 14, thumb link 332 may comprise a palmar end and a dorsal end. The palmar end of thumb link 332 may comprise opposing walls with holes extending therethrough along the medial-lateral axis. The dorsal end of thumb body 318 may be located between or on either side of the opposing walls of the palmar end of thumb link 332. The dorsal end of thumb link 332 also may comprise opposing walls with holes extending therethrough. Thumb connector 333 is rotated in FIG. 14, but still comprises a palmar end and a dorsal end. The palmar end of thumb connector 333 may comprise a rectangular shape receivable between or on either side of the opposing walls of the dorsal end of thumb link 332 and a hole extending therethrough. The dorsal end of thumb connector 333 may comprise a circular shape with a hole extending therethrough.

Slider frame 304 may comprise a structure with a complex 3D geometry made from a polymeric material utilizing an additive manufacturing method, making it a polymeric component. Aspects of slider frame 304 may be different from slider frame 104 and one-piece adaptive grasp plate 15 described in the '460 application. As shown in FIGS. 11, 12, 13, and/or 14, slider frame 304 may comprise proximal holes 322, distal holes 323, a channel 324, a thumb hinge portion 325, and a locking structure 313D. Proximal holes 322 (e.g., shown in FIG. 12) may be aligned with distal holes 323 (e.g., shown in FIG. 14) along the proximal-distal axis to define passages extending through slider frame 304. Channel 324 may comprise surfaces on the palmar side of slider frame 304 that are shaped to removably attach the actuator to slider frame 304. As shown in FIG. 12, thumb hinge portion 325 may comprise protrusion extending dorsally outwardly from slider frame 104 and a hole extending through the protrusion.

Locking structure 313D may comprise a dorsal portion of a back-lock mechanism operable to switch prosthetic hand apparatus 300 between a free grasp state, and a locked grasp state. The polymeric components of prosthetic hand apparatus 300 also may comprise a cover 312 operable to enclose interior cavity 308. As shown in FIG. 14, cover 312 may comprise a locking structure 313P operable as a palmar portion of the back-lock mechanism. The dorsal and palmar portions of the back-lock mechanisms may be operable as described in the '460 application.

Force transfer elements 305 may comprise metallic components operable to transfer forces between the prosthetic components of hand body 302, digits 303, and slider frame 304 when 300 is actuated. As shown in FIGS. 11 and 12, force transfer elements 305 may comprise operational linkages for finger digits 314, biasing elements for finger digits 314, guide elements for slider body 304, and a portion of the operational linkage for thumb digit 315. The metallic components of force transfer elements 305 may comprise 2D shapes made from a metallic material utilizing a rapid manufacturing method, making them metallic components. Similar to as shown in FIG. 14, the 2D shapes may be cut from single metal plate 700 with the rapid manufacturing method, such as laser cutting or water cutting, so that each 2D shape has a precision cut outer perimeter with a uniform thickness.

The operational linkages for each finger digit 314 may comprise a third finger link 326, fourth finger links 327, a finger coupler 328, and a slider plate 329. Third finger link 326 and fourth finger links 327 may be similar to counterpart elements of prosthetic hand apparatus 100 described above. As shown in FIGS. 11-14, finger coupler 328 may comprise a distal end, an interior portion, and a proximal end. The 2D shape of finger coupler 328 may be aligned with the palmar-dorsal axis so that the uniform thickness of its distal end may be received between fourth finger links 327. The distal and interior portions of finger coupler 328 may comprise holes extending therethrough. The proximal end of finger coupler 328 may comprise opposing flanges extending outwardly therefrom, giving it an inverted "T" shape.

As shown in FIG. 14, the operational linkages for finger digits 314 also may comprise finger springs 314S and biasing springs 314B. Springs 314S and 314B may comprise coil springs made of a metallic material, making them metallic components of prosthetic hand apparatus 300. Springs 314S and 314B may be formed by any method for making coil springs out of a metallic material, including bending and/or heating. As shown in FIGS. 12, 13 and 14, each finger spring 314S may comprise an outer diameter receivable in distal holes 323 of slider frame 304 and interior diameter sized to receive the interior portion of one finger coupler 328. The opposing flanges of finger coupler 328 may define a width greater than the inner diameter of springs 314S, allowing springs 314S to be retained between a distal surface of the opposing flanges and a proximal surface of slider plate 329. Biasing springs 314B may be fixedly engaged with hand body 302 and slider frame 304 and operable to bias digits 303 toward the open position shown in FIG. 11. As shown in FIGS. 13 and 14, a first biasing spring 314B may be mounted to lateral portions of hand body 302 and slider frame 304 and a second biasing spring 314B may be mounted to medial portions of body 302 and frame 304. As shown in FIG. 13, an interior cavity 308 of slider frame 304 may comprise a lateral cut-out for the first biasing spring 314B and a medial cut-out for the second biasing spring 314B.

As shown in FIG. 14, the guide elements for slider frame 304 may comprise a pair of elongated rods 331 inserted through the aforementioned holes extending through the proximal portion of hand body 302, the proximal and distal surfaces of its interior cavity 308, and the dorsal portions of slider frame 304. Each rod 331 may comprise a metallic component of prosthetic hand apparatus 300. For example, like each rod 131, each rod 331 also may comprise a rectangular cross-section cut from a metallic base material like the other metallic components of prosthetic hand apparatus 100 and/or a circular cross-section made by conventional means. As shown in FIG. 14, rods 331 may be similarly contained inside the holes when base 301 is engaged with hand body 302.

In addition to thumb link 332 and thumb connector 333, the aforementioned portion of the operational linkage for thumb digit 315 may comprise a thumb pivot plate 334 similar to thumb pivot plate 136 of prosthetic hand apparatus 100 described above.

Slider plate 329 may be engageable with the distal surface of slider frame 304. As shown in FIGS. 12, 13 and 14, slider plate 329 may comprise screw holes 335, slots 336, finger coupler holes 337, and a thumb hinge portion 338. Screw holes 335 may be aligned with screw holes extending distally into slider frame 304. Slots 336 may be shaped to receive rods 331 so that slider plate 329 and rods 331 are operable to limit movements of slider frame 304 along the medial-lateral axis when moving along the proximal-distal axis. Finger coupler holes 337 may be aligned with proximal holes 322 of slider frame 304 when slider plate 329 is engaged therewith. As shown in FIG. 14, each finger coupler hole 337 may have a rectangular cross-section that is larger than a rectangular cross-section of finger coupler 328 and smaller than that of the opposing flanges of finger coupler 328. Thumb hinge portion 338 may comprise a protrusion extending outwardly from slider plate 329 and a hole extending through the protrusion.

Methods of assembling prosthetic hand apparatus 300 are now described with reference to an assembly method 400 comprising steps that are similar to assembly method 200, but within the 400 series of numbers. As shown in FIG. 20, assembly method 400 may comprise: (i) assembling a finger digit assembly 340 (a step 410); (ii) assembling a slider frame assembly 341 (a step 420); (iii) assembling a thumb digit assembly 342 (a step 430); and (iv) assembling finger digit assembly 340 together with thumb digit assembly 341, slider frame assembly 341, and hand body 302 (a step 440). As above, each of steps 410-440 may comprise intermediate steps in keeping with the structural and functional descriptions of prosthetic apparatus 100 set forth in this disclosure.

An example of finger digit assembly 340 is shown in FIGS. 12 and 14. As shown, step 410 may comprise assembling finger digit assembly 340 by rotatably engaging first finger links 316, second finger links 317, third finger links 326, fourth finger links 327, and finger couplers 328. Each rotational engagement may function similar to a pinned connection, in which a metal pin or equivalent rotational surface is inserted through the various holes described above. For example, step 410 may comprise steps 411-414 that are similar to steps 211-214 described above with reference to prosthetic hand apparatus 100, plus: (e) inserting finger couplers 328 into proximal holes 322 of slider frame 304 (a step 415); (f) inserting finger springs 314S into distal holes 323 of slider frame 304 so that finger couplers 328 are located inside finger springs 314S (a step 416); (g) receiving the distal ends of finger couplers 328 in finger coupler holes 337 of slider plate 329 (a step 417); and (h) receiving the distal ends of finger couplers 328 between the proximal ends of fourth finger links 327, aligning their respective holes, inserting pins through the holes, and securing the pins thereto so that finger springs 314S are contained between slider plate 329 and the opposing flanges of the proximal ends of finger couplers 328 (a step 418).

An example of slider frame assembly 341 is shown in FIGS. 12, 13 and 14. As shown, step 420 may comprise assembling slider frame assembly 341 by fixedly engaging slider frame 304 with slider plate 329. Step 420 may comprise, after step 418 described above: (a) positioning the proximal surface of slider plate 329 on the distal surface of slider frame 304 to contain finger springs 314S between the proximal surface of slider plate 329 and the opposing flanges of finger coupler 328 (a step 421); (b) aligning screw holes 335 of slider plate 329 with holes extending into slider frame 304 (a step 422); (c) inserting screws through holes 335 (a step 423); (d) engaging threads of the screws with the holes of slider frame 304 (a step 424); (e) inserting pins through the holes extending through the interior portions of finger couplers 328 and securing the pins thereto (a step 425); and (f) maintaining surfaces of the pins against the distal surface of slider plate 329 with forces applied by the finger springs 314S (a step 426).

An example of thumb digit assembly 342 is shown in FIG. 11. In keeping therewith, step 430 may comprise assembling thumb digit assembly 342 by rotatably engaging thumb body 318, thumb base 319, thumb link 332, and thumb connector 333, and thumb plate 334. Step 430 may comprise: (a) receiving the proximal end of thumb body 318 between the opposing walls of the palmar end of thumb link 332, aligning their respective holes, inserting pins through the holes, and securing the pins thereto (a step 431); (b) receiving the palmar end of thumb connector 333 between the opposing walls of the dorsal end of thumb link 332, aligning their respective holes, inserting pins through the holes, and securing the pins thereto (a step 432); and (c) receiving the interior portion of thumb body 318 between the opposing walls of the distal end of thumb base 319, aligning their respective holes, inserting pins through the holes, and securing the pins thereto (a step 433).

Once finger digit assembly 340, slider frame assembly 341, and thumb digit assembly 342 have been assembled, step 440 may further comprise engaging those elements to form prosthetic apparatus 300. For example, step 440 may comprise: (a) inserting the dorsal end of thumb connector 333 between hinge portions 325 and 338, aligning their respective holes, inserting a pin through the holes, and securing the pin thereto (a step 441); (b) rotatably engaging hand body 302 with slider frame assembly 341 and thumb digit assembly 342 by receiving the proximal ends of second finger links 317 between the opposing walls of finger digit attachment portions 307, aligning their respective holes, inserting pins through the holes, and securing the pins thereto (a step 442); (c) rotating slider frame assembly 341 and thumb digit assembly 342 to locate slider frame 304 inside of interior cavity 308 and position the rotational surface of thumb base 319 adjacent the rotational surface of thumb pivot 310 (a step 444); (e) inserting the dorsal end of thumb pivot plate 334 into thumb recess 311 and positioning the palmar end of thumb pivot plate 334 on the rotational surface of thumb base 319 (a step 445); (f) inserting screws through hand body 302 and into the holes of the palmar end of thumb pivot plate 334 and thumb recess 311 (a step 446); (g) inserting screws through the holes of the dorsal end of thumb pivot plate 334 and the rotational surface of thumb pivot 310 (a step 447); (h) receiving rods 331 in the various holes and slots 336 described above and securing base 301 to hand body 302 to contain rods 331 therein (a step 448); and (i) positioning cover 312 over interior cavity 308 and securing cover 312 to hand body 302 (a step 449).

Once prosthetic apparatus 300 has been assembled according to method 400 described above (or its equivalent), then it may be utilized to grip objects with digits 303. Force transfer elements 305 may be configured for different types of grips. For example, in keeping with above, force transfer elements 305 may be configured to perform an "adaptive grip" in which a first portion of finger digits 314 are moved toward hand body 302 at a first rate, a second portion of digits 314 are moved toward hand body 302 at a second rate, and the first rate is faster than the second rate so that digits 303 close in more hand-like manner.

For prosthetic apparatus 300, when the actuator is pulled in a proximal direction with a proximally directed force, it will pull slider frame 304 proximally, causing force transfer elements 305 to close finger digits 314 with a grasping force that is proportionate to the proximally directed force. When finger digits 314 come into contact with an object, finger springs 314S may compress an initial amount against the proximal side of slider plate 329. This will allow finger digits to open slightly. Each finger digit 314 may move semi-independently, allowing them to be in various positions of closure, much like finger digits 114 of prosthetic hand apparatus 100. This allows finger digits 314 to adaptively conform around exterior surfaces of the object and obtain a better grip therewith.

Figure 23:
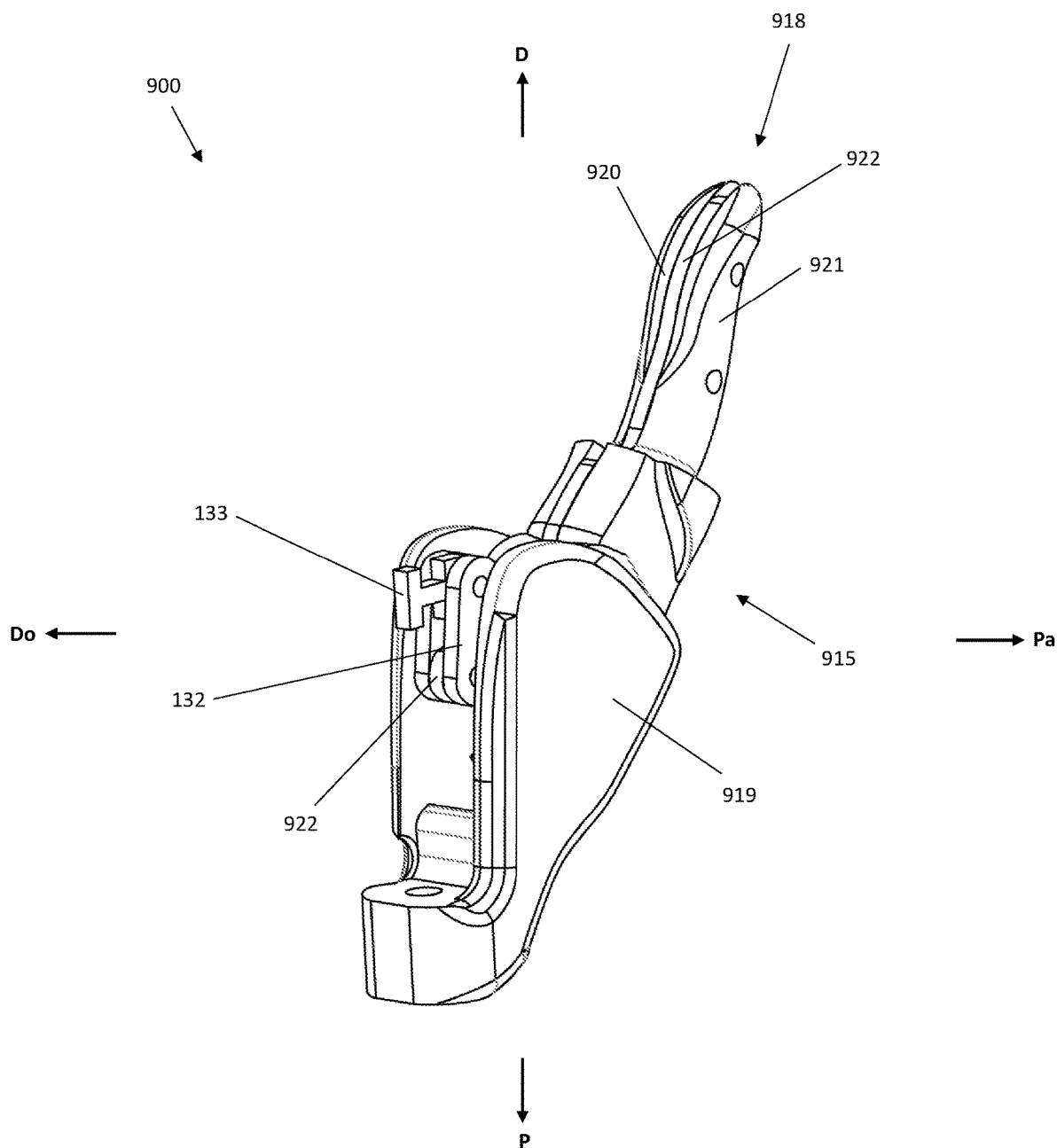
FIG. 23 depicts a perspective view of another exemplary thumb assembly of the FIG. 1 prosthetic hand apparatus.

Prosthetic hand apparatus 900 may comprise prosthetic hand apparatus 100 described above but with a thumb digit 915. As shown in FIG. 23, thumb digit 915 may comprise a thumb body 918 and a thumb base 919. Aspects of thumb body 918 and thumb base 919 may be similar to thumb body 118 and thumb base 119 described above. For example, each of thumb body 918 and thumb base 919 may comprise a structure with a complex 3D geometry made from a polymeric material utilizing an additive manufacturing method, meaning that they may include one or more polymeric components.

Figure 24:
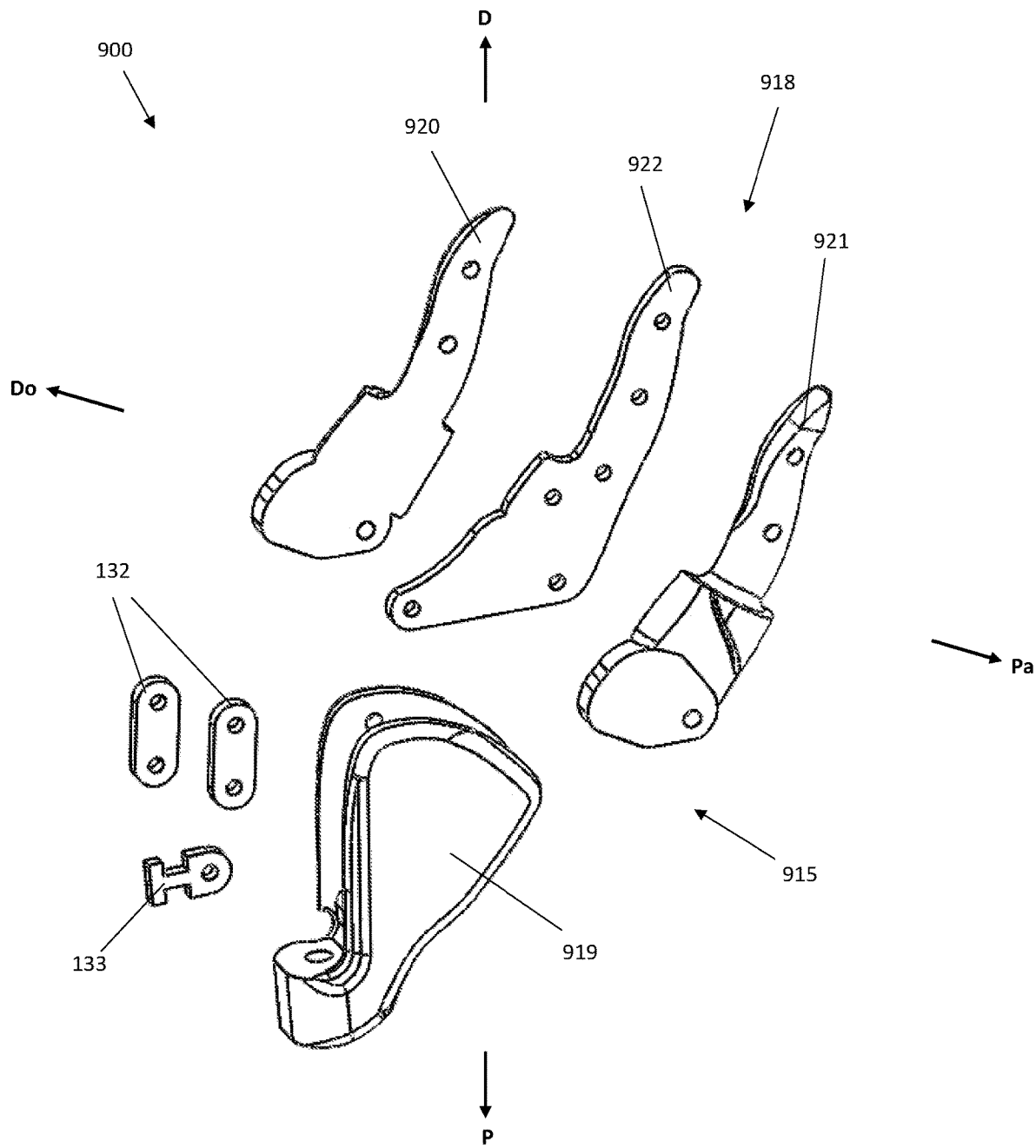
FIG. 24 depicts an exploded view of the FIG. 23 prosthetic hand apparatus.

Thumb body 918 may comprise one or more polymeric components and a metallic component. As shown in FIG. 23, thumb body 918 may comprise a first thumb side 920, a second thumb side 921, and a thumb link 922. First and second thumb sides 920, 921 may be separate, such that the one or more polymeric components of thumb body 918 may comprise two different complex 3D geometries defining thumb sides 920, 921. As shown in FIGS. 23 and 24, first thumb side 920 may be assembled together with second thumb side 921 to define a distal end and an interior portion of thumb body 918. The distal end or tip of thumb body 918 may comprise a fingernail and a grip surface like that of thumb body 118. The interior portion of thumb body 918 may be thicker. Various holes may extend through thumb first and second thumb sides 920 and 921, including distal holes at their distal ends and an interior hole at their proximal ends (which are located at or adjacent to the interior portion of thumb link 922 as shown in FIG. 24).

Thumb link 922 may comprise a 2D shape made from a metallic material utilizing a rapid manufacturing method, making it a metallic component. As shown in FIG. 24, thumb link 922 may be located between first thumb side 920 and second thumb side 920 to define a rigid, internal structure of thumb body 918. Thumb link 922 may comprise a distal end, an interior portion, and a proximal end. Various holes may extend through thumb link 922, including distal holes at its distal end, an interior hole in its interior portion, and a proximal hole in its proximal portion.

Aspects of thumb base 919, like thumb base 119, may function similar to a first metacarpal of the human thumb. As shown in FIG. 23, thumb base 919 may comprise a distal end and a proximal end. The distal end of thumb base 919 may comprise opposing walls with holes extending therethrough. The thickened proximal end of first and second thumb plates 920, 921 (and thus the interior portion of thumb body 918) may be located between the opposing walls of the distal end of thumb base 919. The proximal end of thumb base 919 may be similar to that of thumb base 119.

Prosthetic hand apparatus 900 may comprise an operational linkage for thumb digit 915 that is operable to convert a linear movement of slider frame 104 relative to hand body 102 into a rotational movement of thumb body 918 relative to hand body 102. The operational linkage for thumb digit 915 may comprise piston plates 132 and a thumb link 133 as described above. As similarly shown in FIGS. 23 and 24, piston plates 132 may comprise an opposing pair of 2D shapes, including a lateral plate and a medial plate that are spaced apart from one another along the medial-lateral axis, each having a distal end and a proximal end. The distal and proximal ends of piston plates 132 may comprise holes extending therethrough. The 2D shapes of piston plates 132 may be aligned with thumb base 919 so that their uniform thickness may be received between the opposing walls of the distal end of thumb base 919. As similarly shown in FIGS. 23 and 24, thumb link 133 may comprise the same dorsal end and palmar end as described above.

Prosthetic hand apparatus 900 may be assembled with a modified version of assembly method 200, in which aspects of steps 230 and 240 are modified to accommodate thumb digit 915. For example, a modified step 230 may comprise: (a) locating thumb link 922 between first and second thumb plates 920, 921, aligning the distal holes extending therethrough, inserting pins through the distal holes, and securing the pins thereto to form thumb body 918 by fixedly engaging first and second thumb sides 920, 921 with thumb link 922; (b) receiving the proximal end of thumb link 922 between the distal ends of piston plates 132, aligning the interior hole of thumb link 922 with the holes at the distal ends of piston plates 132, inserting pins through the holes, and securing the pins thereto to rotatably engage thumb body 918 with piston plates 132; (c) receiving the palmar end of thumb link 133 between the proximal ends of piston plates 132, aligning their respective holes, inserting pins through the holes, and securing the pins thereto to rotatably engage piston plates 132 with thumb link 133; and (d) receiving the thickened proximal portion of thumb body 918 between the opposing walls of the distal end of thumb base 919, aligning the interior hole of thumb body 918 (formed by the proximal hole of first thumb side 920, the proximal hole of second thumb side 921, and central hole of thumb link 922) with the holes extending through the opposing walls of thumb base 919, inserting a pin through the holes, and securing the pin to thumb base 919 to rotatably engaged thumb body 918 therewith.

Figure 15:
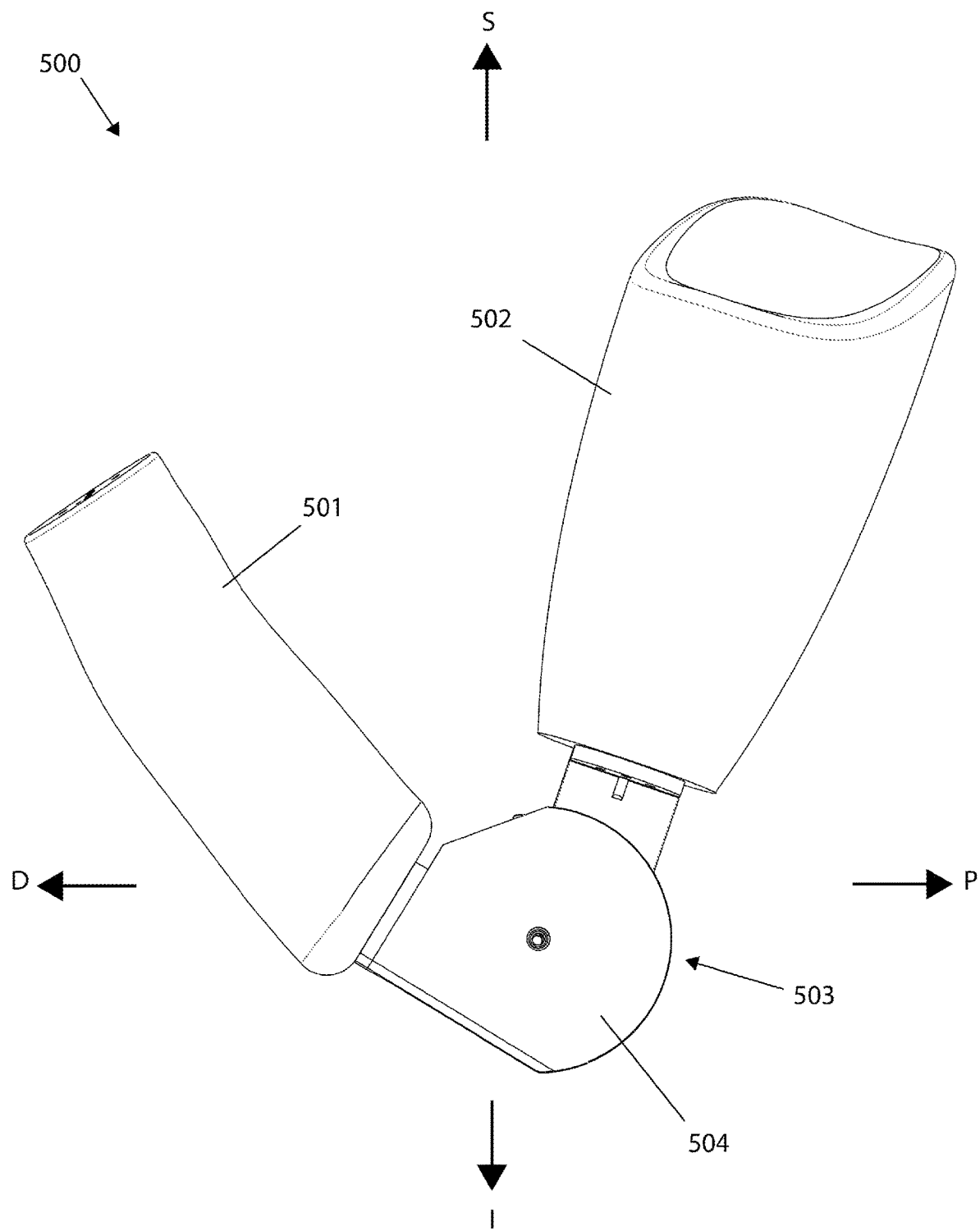
FIG. 15 depicts a perspective view of an exemplary arm assembly comprising a lower arm portion, an elbow, and an upper arm portion
Figure 16:
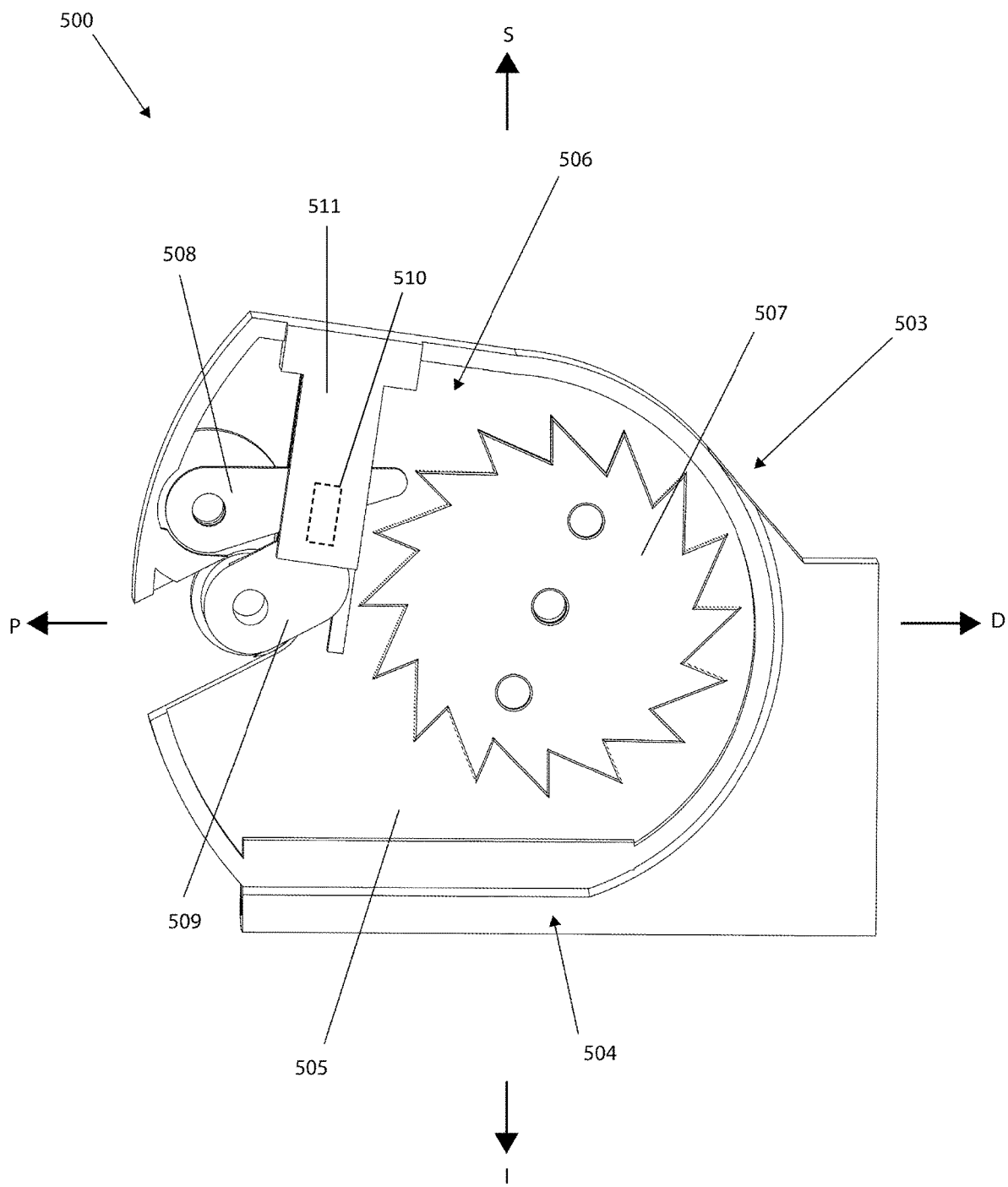
FIG. 16 depicts a cross-sectional view of the FIG. 15 elbow showing exemplary force transfer elements that are selectively engageable with one another.

Aspects of prosthetic hand apparatus 100, 300, and 900. may be applicable to different types of prosthetics. To provide an example, aspects of an exemplary prosthetic apparatus 500 are now described. As shown in FIGS. 15 and 16, prosthetic apparatus 500 may restore elbow functionality for someone missing their arm above the elbow. Components of prosthetic apparatus 500 may be similarly manufactured with low-cost manufacturing methods to help a human subject with a partial limb regain some normal functions. For example, like prosthetic hand apparatus 100, 300, and 900 described above, prosthetic apparatus 500 also may comprise combinations of polymeric components, metallic components, and engagement elements operable therewith.

As shown in FIGS. 15 and 16, prosthetic apparatus 500 may comprise a lower arm portion 501, an upper arm portion 502, and an elbow 503. As shown in FIG. 15, lower arm portion 501 may comprise a distal end engageable with prosthetic hand apparatus 100 and a proximal end engageable with elbow 503 and upper arm portion 502 may comprise a distal end engageable with elbow 503 and a proximal end with a socket sized to receive a partial limb of the user. Lower arm portion 501 and upper arm portion 502 may comprise structures with complex 3D geometries made from a polymeric material utilizing an additive manufacturing method, making them polymeric components like those of prosthetic hand apparatus 100, 300, and 900. Upper arm portion 502 may be custom made to the user's limb anatomy by use of 3D-scanning or other similar methods.

Aspects of elbow 503 may resemble a human elbow joint and appear to operate similarly. As shown in FIG. 16, elbow 503 may comprise an elbow body 504, an interior cavity 505, and force transfer elements 506. Elbow body 504 may comprise exterior surfaces resembling an elbow and interior surfaces defining interior cavity 505. In keeping with above, elbow body 504 also may comprise a structure with a complex 3D geometry made from a polymeric material utilizing an additive manufacturing method, making it another polymeric component.

Force transfer elements 506 may comprise polymeric components operable through openings of elbow body 504 and metallic components operable from within interior cavity 505 of elbow body 504. As shown in FIG. 16, force transfer elements 506 may comprise a combination of polymeric and metallic components, including a ratchet 507, a pawl 508, an elbow release 509, an elbow spring 510, and an elbow spring structure 511. Rachet 507 and pawl 508 may comprise 2D shapes made from a metallic material utilizing a rapid manufacturing method, making them metallic components. As shown in FIG. 16, rachet 507 may comprise a circular shape with teeth, and the circular shape may be rotatably engaged with elbow body 504 inside of interior cavity 505. As also shown in FIG. 16, pawl 508 may comprise a proximal end rotatably engaged with elbow body 504 and a distal end engageable with the teeth of ratchet 507. Elbow release 509 may comprise polymeric components extending through openings of elbow body 504, including a lever portion positioned outside cavity 505 and a drive portion positioned inside cavity 505. As shown in FIG. 16, elbow spring structure 511 may comprise a reinforced portion of elbow body 504 (e.g., show as having a "T" shape) defining an interior channel. Elbow spring 510 (e.g., shown conceptually with dotted lines) may comprise a coil spring that is attached to elbow body 504 and pawl 508 inside of the interior channel of elbow spring structure 511 so that pawl 508 is biased toward rachet 507.

In operation, a human subject may manually move lower arm portion 501 and prosthetic hand apparatus 100, 300 engaged therewith in an upward direction by physically lifting lower arm portion 501 or by pushing lower arm portion 501 against an object, such as a table. For example, the subject may lift prosthetic hand apparatus 100, 300 between multiple different positions to assist with certain tasks, such as when lifting the hand towards their face to eat. When the subject lifts lower arm portion 501 into position, ratchet 507 may rotate relative to elbow body 504 until one of the teeth of ratchet 507 are engaged with distal end of pawl 508 so that lower arm portion 501 cannot be lowered. As shown in FIG. 16, pawl 508 may be rotatably connected to elbow body 504 at a rotation point that allows pawl 508 to rotate when ratchet 507 pushes against it. Elbow spring 510 may be engaged with elbow body 504 and pawl 508 inside of elbow spring structure 511. The distal end of pawl 508 may be lifted by the one tooth of ratchet 507, expanding elbow spring 510. After ratchet 507 rotates past a certain point, pawl 508 will become engaged with another one of the teeth of rachet 507 and return to its normal starting position due to forces applied to pawl 508 by elbow spring 510 as it contracts.

Ratchet 507 and pawl 508 may be engaged so that lower arm portion 501 and upper arm portion 502 are not free to rotate with respect to each other. In this instance, elbow release 509 may be operable to disengage ratchet 507 and pawl 508. As shown in FIGS. 15 and 16, to move lower arm portion 501, the user may push on elbow release 509 to disengage pawl 508 from ratchet 507. For example, the tip of elbow release 509 may be operable to push pawl 508 away from the tooth of ratchet 507 so that lower arm portion 501 and prosthetic hand apparatus 100, 300 engaged therewith may rotate relative to upper arm portion 502. The weight of lower arm portion 501 and apparatus 100, 300 may desirably cause elbow 503 to lower arm portion 501 and apparatus 100, 300 to a starting position with additional forces applied thereto, making it easy to reconfigure prosthetic apparatus 500.

Figure 21:
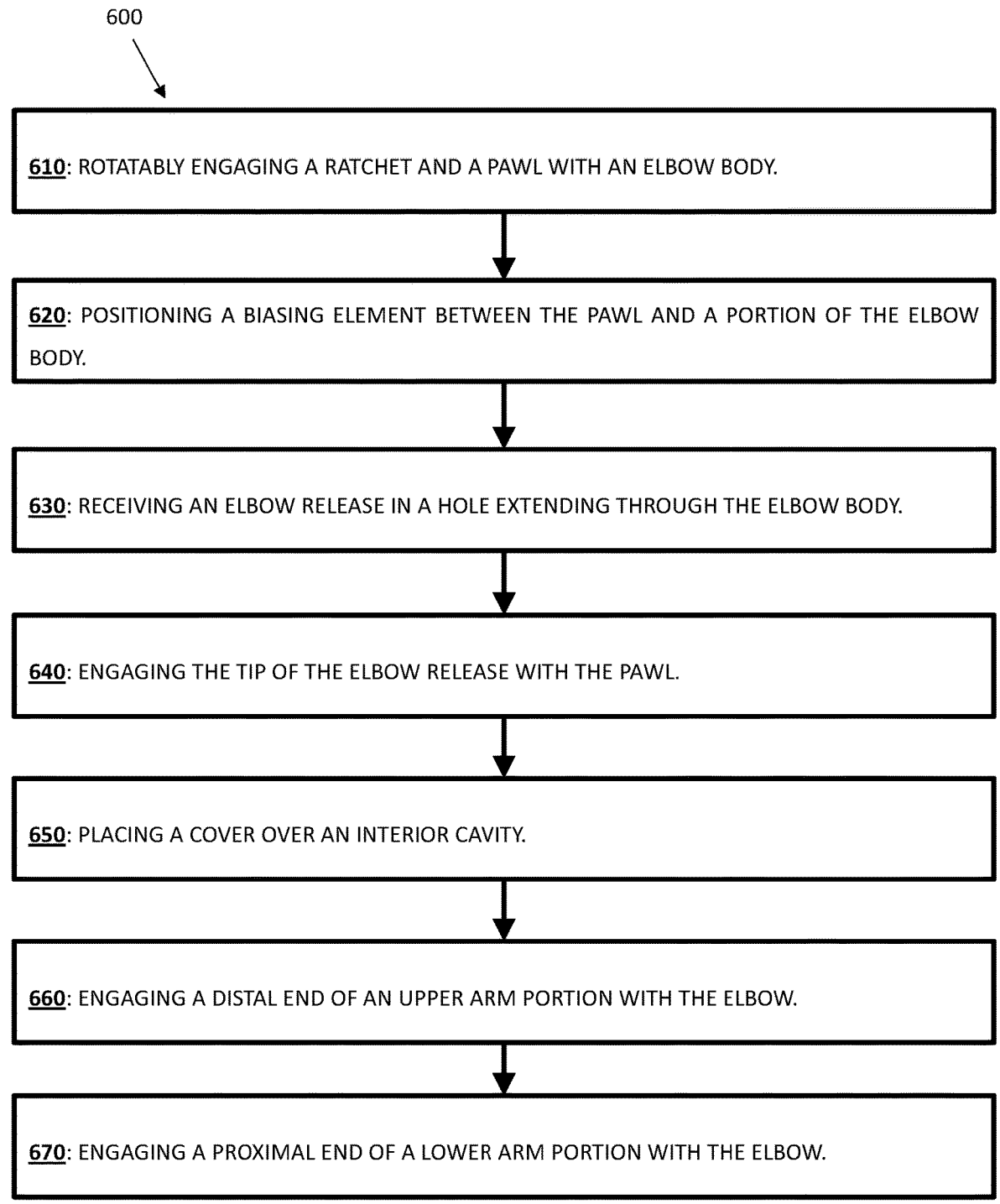
FIG. 21 depicts yet another exemplary assembly method.

A method of assembling prosthetic apparatus 500 are now described with reference to an assembly method 600 comprising steps that are similar to assembly methods 200, 400, but within the 600 series of numbers. As shown in FIG. 21, assembly method 600 may comprise: (i) rotatably engaging ratchet 507 and pawl 508 with elbow body 504 (a step 610); (ii) positioning a biasing element (e.g., a spring) between pawl 508 and an portion of elbow body 504 (a step 620); (iii) receiving elbow release 509 in a hole extending through elbow body 504 (a step 630); (iv) engaging the tip of elbow release 509 with pawl 508 (a step 640); (v) placing a cover over interior cavity 505 (a step 650); (vi) engaging the distal end of upper arm portion 502 with elbow 503 (a step 660); and (vii) engaging the proximal end of lower arm portion 501 with elbow 503 (a step 670). As above, each of steps 610-670 also may comprise intermediate steps in keeping with the structural and functional descriptions of prosthetic apparatus 500 set forth in this disclosure.

Figure 22:
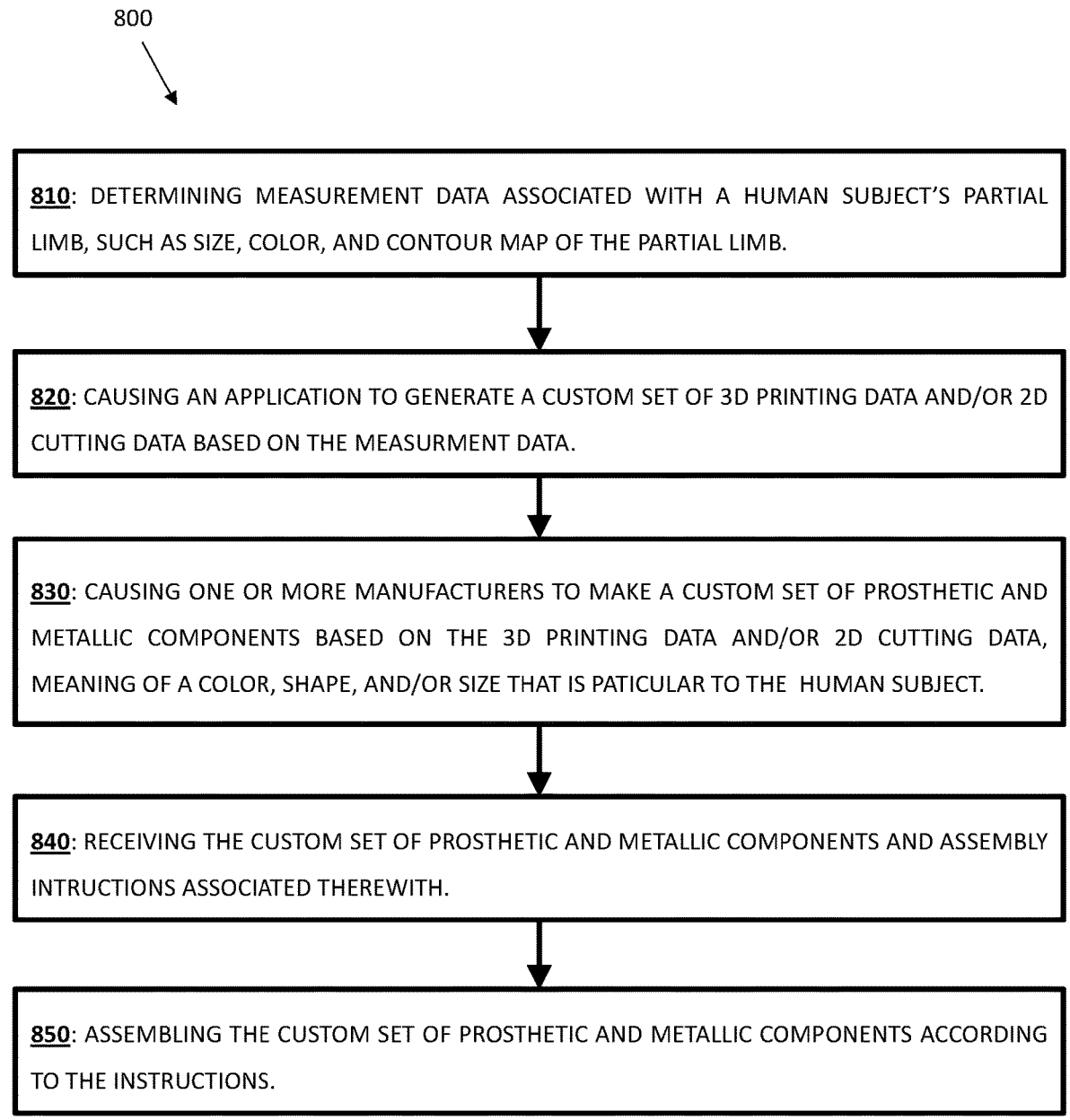
FIG. 22 depicts an exemplary procurement method.

Certain aesthetic, economic, and performance benefits may be realized with prosthetic apparatus 100, 300, 500, and 900 and/or assembly method 200, 400, and 600. Aesthetically, the exterior surfaces of hand body 102, 302, digits 103, 303, cover 112, 312, lower arm portion 501, upper arm portion 502, and/or elbow 503 may have shapes defined primarily by the prosthetic components of prosthetic apparatus 100, 300, 500, and/or 900, making those components mass customizable according to visual characteristics established by the human subject. In this way, as shown in FIG. 22, each human subject or an agent thereof may be able to order a custom one of prosthetic apparatus 100, 300, 500, and/or 900 with a procurement method 800 comprising: (i) determining (e.g. with a 3D scanner) measurement data associated with their partial limb, such as a color, size, and contour map of the partial limb (a step 810); (ii) causing an application to generate a custom set of the above-described 3D printing data and/or 2D cutting data based on the measurement data (a step 820); (iii) causing one or more manufacturers to make a custom set of the above-described prosthetic and metallic components based on the 3D printing data and/or 2D cutting data, meaning of a color, shape, and/or size that is particular to the subject (a step 830); (iv) receiving the custom set of prosthetic and metallic components and assembly instructions associated therewith (a step 840); and (v) assembling the custom set of prosthetic and metallic components according to the instructions (a step 850), each of which may include intermediate steps in keeping with the examples described in this disclosure. Any degree of mass-customizability may be realized in this manner. Because of this customizability, the components of prosthetic apparatus 100, 300, 500, and/or 900 may be color matched, shape matched, and/or size matched, meaning scaled down to a smaller size for use by smaller subjects (e.g., children) or scaled up to a larger size for larger subjects (e.g., adults). The performance benefits of prosthetic apparatus 100, 300, 500, and/or 900 may thus be more universally applicable to a greater number of subjects around the world.

Some benefits of prosthetic apparatus 100, 300, 500, and/or 900 as well as assembly methods 200, 400, and/or 600 may be derived from how their respective prosthetic and the metallic components are assembled and/or combined. Performance wise, the shapes and configurations of the polymeric and metallic components described above may allow prosthetic apparatus 100, 300, 500, and 900 to be stronger and more durable than it otherwise could be due to enhanced strengths of the metallic materials relative to that of the polymeric materials. As described and shown herein, the polymeric components of prosthetic apparatus 100, 300, and/or 900 may be located in areas where internal stresses associated with moving digits 103, 303 are low, such as on first finger links 116, 316 and second finger links 117, 317; and the metallic components of prosthetic apparatus 100, 300, and/or 900 may be located in areas of where the internal stresses associated with moving digits 103, 303 are high, such as on rocker 130 of apparatus 100, slider frame 304 of apparatus 300, and the respective operational linkages for finger digits 114, 314 and thumb digit 115, 315, 915. Because of thumb link 922, the location of the metallic components of prosthetic hand apparatus 900 may increase a strength of thumb digit 915 while maintaining its cosmetic appearance with the polymeric components. As shown in FIGS. 23 and 24, thumb digit 915 may thus be operated and closed with actuation forces that are transferred with the metallic components of prosthetic hand apparatus 900.

Prosthetic apparatus 500 may similarly utilize the polymeric components for outward appearances and to position the metallic components at locations where the internal stresses are highest. For example, elbow 503 may be operable to lift lower arm portion 501 and prosthetic apparatus 100, 300, and/or 900 attached thereto, thereby generating internal stresses in the form of a torque applied to operational components 506. Because they are made from metallic components, ratchet 507 and pawl 508 may stay operatively engaged when the torque is applied and be strong enough to accommodate a higher applied torque than would otherwise be possible if ratchet 507 and pawl 508 were made of polymeric components.

The above-described rotational engagements between the polymeric components and the metallic components of prosthetic apparatus 100, 300, 500, and/or 900 may evenly transfer forces from the metallic components to the polymeric components by dividing forces between at least two separate holes and over the respective internal surface areas of the two separate holes. For example, each opposing wall of the palmer portion of first finger link 116, 316 may be substantially thicker (e.g., 2-3× thicker) than the uniform thickness of the distal end of third finger link 126, 326, and the pin inserted between these particular holes of links 116, 316 and 126, 326 may span between the medial and lateral sides of first finger link 116, allowing forces transferred between links 116, 316 and 126, 326 to be more evenly distributed over a larger internal surface area, making it less likely or impossible for the resulting stresses to exceed the corresponding strengths of the polymeric materials during normal usage of prosthetic apparatus 100, 300. The portions of elbow body 504 providing rotational supports for ratchet 507 and pawl 508 may be similarly thickened or otherwise reinforced. Any supports defined by and/or thickness of the polymeric components may be similarly configured.

Some benefits of prosthetic apparatus 100, 300, 500, and/or 900 as well as assembly methods 200, 400, and/or 600 may be derived from the way in which the polymeric components are made. As described above, each polymeric component may be manufactured with an additive manufacturing method, like 3D printing, in which the component is built up layer-by-layer. These methods, particularly 3D printing, may allow for the efficient and rapid manufacture of complex 3D shapes having a custom fit with a particular subject, also known as mass-customization, something that is typically not economically feasible with conventional manufacturing methods more suitable for large runs, such as machining, injection molding, and casting. For example, 3D printing the polymeric components to fit the subject may be less expensive and faster because there is no need for expensive molds, dies, jigs, fixtures, and/or other traditional manufacturing infrastructure requiring upfront costs and set up time.

As a further example, when 3D printed, the polymeric components also may be lighter in weight when compared to components made from other traditional manufacturing methods by having an internal infill density less than 100%. This can make some 3D printed components structurally weaker than similar components made by traditional manufacturing methods. Prosthetic apparatus 100, 300, 500, and/or 900 may overcome this disadvantage by positioning the metallic components to handle most of the internal stresses, making it easier to accommodate the structural limitations of the polymeric components when 3D printed. The resulting stress distribution may allow the polymeric components to be reduced in some areas, making them even smaller and/or lighter so that prosthetic apparatus 100, 300, 500, and/or 900 may have both an increased strength and a reduced overall weight relative to a comparable apparatus made entirely with polymeric components made by any means.

Some benefits of prosthetic apparatus 100, 300, 500, and/or 900 may be derived from the way in which the metallic components are made. For example, flat metal plates like the 2D shapes described above may be preferable to metal parts having complex 3D shapes because the 2D shapes may be easily and inexpensively cut from metallic materials by rapid manufacturing methods, such as laser cutting or water cutting. These traditional methods may be utilized to efficiently create flat components like the above-described 2D shapes using many different kinds of strong materials, such that the metallic components described herein may comprise any type of metallic materials (e.g., like steel, hardened steel, steel alloys, metallic alloys, etc.) and/or any type of non-metallic materials, including any composite materials (e.g., carbon fiber or Kevlar reinforced materials), inorganic materials (e.g., ceramics) and/or other polymeric materials (e.g., any non-printable ultra-high molecular weight polyethylene fibers). Many of these materials cannot be 3D printed and instead must be shaped into complex 3D shapes using more conventional methods, meaning that it may not be economically feasible to incorporate them into prosthetic apparatus 100, 300, 500, and/or 900 without cutting them into the 2D shapes described herein.

A known disadvantage of many rapid manufacturing methods is that the resulting parts must be cut from a flat sheet of material (e.g., like sheet 700) due to the x-y motion of the rapid manufacturing method, meaning that parts must be generally flat structures that may be inherently difficult to bend. The metallic components of prosthetic apparatus 100, 300, 500, and/or 900 may overcome this disadvantage by comprising 2D shapes with unique sets of curves, holes, and/or functional orientations operable to transfer forces between corresponding sets of curves, holes, and/or functional orientations of the polymeric components of apparatus 100, 300, 500, and/or 900. The incorporation of the above-described 2D and 3D shapes into functional biological replacements like prosthetic apparatus 100, 300, 500, and/or 900 may require significant experience and skill in the art, such that any structural aspects of the various sets of curves, holes, and/or functional orientations described above may be claimed.

As described herein, prosthetic apparatus 100, 300, 500, and/or 900 may be manufactured utilizing two different types of rapid manufacturing methods (such as 3D printing and/or precision cutting with lasers or water) and assembled at a significantly lower cost, resulting in a prosthetic apparatus (e.g., a terminal unit) offering: (a) high functionality; (b) a durable construction that will not break during typical use; (c) a customizable size that is right-sized and thus suitable for a particular subject; and (d) a customizable anthropometric (natural-looking) appearance that is also appropriate for its size. The particular type of manufacturing methods may be selected based on the local manufacturing capabilities of a particular area.

Aspects of prosthetic apparatus 100, 300, 500, and/or 900 may be similarly packaged, distributed, and/or sold in different types of kits with assembly instructions based on the above-described steps of methods 200, 400, and 600 based on the local manufacturing capabilities of a particular area. In keeping with FIGS. 1-18, an exemplary kit may comprise any one or more of: (a) any combination of the above-described prosthetic and metallic components in a completed form; (b) an amount of polymeric material (e.g., a 3D printable material) with instructions (e.g., 3D printing data) for manufacturing the polymeric components with the polymeric material (e.g., with a 3D printer); and/or (c) a metallic plate (e.g., a stainless steel plate) with instructions (e.g., CNC cutting data) for manufacturing the metallic components with the metallic plate.

Different components for different prosthetics may be manufactured and/or sold together in different embodiments of a kit, making it possible to provide components of (e.g., like those shown in FIGS. 1-18) and assembly instructions for (e.g., like those shown in FIGS. 19-22) a complete prosthetic system suitable for any user based on the descriptions provided herein. The metallic components may be manufactured separately and delivered to the assembling party in an assembly ready form. As shown in FIG. 17, single plate or sheet 700 may be cut based on 2D cutting data for a particular subject with a rapid manufacturing process to define the metallic components of a prosthetic apparatus 100, 300, 500, and/or 900 based on measurement data determined for the subject, such that plate or sheet 700 and each element of apparatus 100, 300, 500, and/or 900 may be mass customized. Each metallic component may remain attached to metal plate or sheet 700 by a frangible portion to simplify production and shipping of the metallic components, allowing for delivery of a flat-packed kit comprising metal plate or sheet 700 and instructions for 3D printing the polymeric components, removing each metallic component from plate or sheet 700, filing down any remainders of the frangible portion, and completing the assembly in keep with methods 200, 400, and/or 600 described above.

Figure 18:
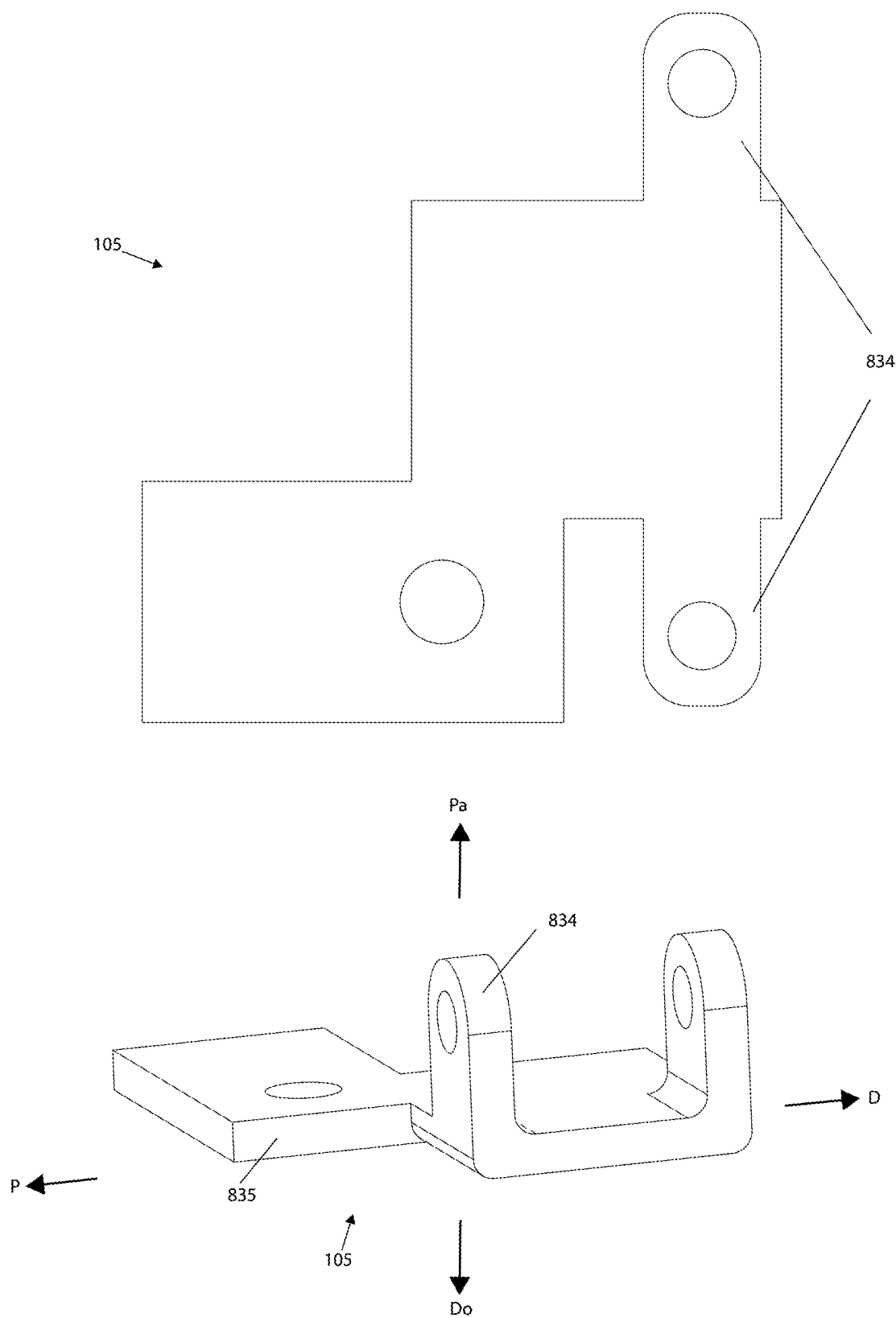
FIG. 18 depicts a plan and a perspective view of an exemplary force transfer element comprising a 2D shape that is deformable into a 3D shape.

As shown in FIG. 18, some metallic components of prosthetic hand apparatus 100, 300, 500, and/or 900 may comprise 2D shapes that are deformable into 3D shapes. As shown in FIGS. 4, 7, 9, and 10, thumb connectors 134 and thumb plate 135 of prosthetic hand apparatus are shown as being 2D shapes that are engageable with one another to form a 3D shape. As shown in FIG. 18, an alternative thumb plate 835 may be cut into a 2D shape having thumb connector portions 834 that are foldable to realize a hinge shape similar to that provided by connectors 134 and plate 135, requiring the assembling party to perform additional folding steps. It is contemplated that many of the 2D and/or 3D shapes described above may be similarly manufactured with additional folding steps.

Utilizing rapid manufacturing methods may be desirable in many instances because it allows for customization of each polymeric and metallic component to meet the needs of a particular subject, but this is not always required. For example, it is possible that some benefits may be obtained with standardized 2D and/or 3D shapes made by other and/or more conventional manufacturing methods if and when it is economically feasible to do so, meaning that aspects described herein may be claimed with either: an apparatus, kit, or system claim reciting structures made by any manufacturing method; or a product-by-process claim reciting particular structures and a particular method of manufacturing the same. Still other aspects may be claimed with method claims reciting limitations that are expressly described in relation to methods 200, 400, 600, and/or 800 or inherent to the various descriptions of prosthetic apparatus 100, 300, 500, and/or 900 provided herein.

While principles of the present disclosure are described herein with reference to illustrative aspects for particular applications, the disclosure is not limited thereto. Those having ordinary skill in the art and access to the teachings provided herein will recognize additional modifications, applications, aspects, and substitution of equivalents all fall in the scope of the aspects described herein. Accordingly, the present disclosure is not to be considered as limited by the foregoing description.

Embodiments in which an exclusive property or privilege is claimed are defined as follows:

1. A system comprising:
    a prosthetic apparatus comprising:
        a plurality of first components manufactured from a first material to define 3D shapes with exterior surfaces resembling digits of a human hand; and
        a plurality of second components manufactured from a second material to define flat plates with uniform thicknesses 2D perimeter shapes,
        wherein the flat plates are rotatbly engageable with one another and the 3D shapes within interior portions of the digits and the body to define force transfer elements comprising first flat plates located in the digits and at least one second flat plate that is located in the body and oriented transversely with the first flat plates,
        wherein the force transfer elements are operable to close the digits around an object responsive to a pull force applied to the force transfer elements, wherein the first material is different from the second material;
    an upper arm prosthetic with a partial limb; and
    a lower arm prosthetic engageable with the prosthetic apparatus,
    wherein:
        the plurality of first components define additional 3D shapes with exterior surfaces resembling a human elbow; and
        the plurality of second components define additional flat shapes that are rotatably engageable with the additional 3D shapes to define additional force transfer elements operable to selectively move the upper arm prosthetic relatic to the lower arm prosthetic.

2. The system of claim 1, wherein the 3D shapes of the plurality of first components are manufactured from the first material with an additive manufacturing method and the plurality of second compoents are manufactured from the second material with a rapid manufacturing method.

3. The system of claim 1, wherein the first material is 3D-printable and the 3D shapes of the plurality of first components are manufactured from the first material with a 3D printer.

4. The system of claim 3, wherein the first material is a polymer or a thermal polymer.

5. The system of claim 3, wherein the plurality of second components are cut from a single flat sheet of the second material using a laser cutter or a water jet cutter.

6. The system of claim 5, wherein one second component the plurality of second components is foldable into an additional 3D shape of the force transfer elements.

7. The system of claim 5, wherein at least two second components of the plurality of second components are engageable with one another to define an additional 3D shape of the force transfer elements.

8. The system of claim 1, wherein the uniform thicknesses of the flat plates is between approximately 0.5 mm and approximately 5 mm.

9. The system of claim 1, wherein the force transfer elements are operable to close the digits around the object with an adaptive grasp and the apparatus comprises one or more springs operable to bias the digits toward an open position of the adaptive grasp.

10. The system of claim 1, wherein a weight of the flat plates is between approximately 5% and approximately 25% of a total weight of the prosthetic apparatus.

11. The system of claim 1, wherein:
    the plurality of first components are 3D printed with the first material using 3D printing data associated with a human subject; and
    the plurality of second components are cut from the second material using 2D cutting data associated with the subject.

12. The system of claim 11, wherein the plurality of second components are cut from a single flat sheet of the second material, using the 2D cutting data, to define frangible portions that removably attach the flat shapes to the single sheet.

13. The system of claim 1, wherein the flat shapes comprise:
    finger link plates with circular holes; and
    a grasp link plate with opposing flanges and a narrowed neck,
    the opposing flanges being insertable through the circular holes along an axis so that the finger link plates are rotatable about the axis relative to the grasp link plate, and
    the opposing flanges having rectagular cross-sections that are receivable in the circular holes so that corners of the rectangular cross-sections are rotatable agains curved interior surfaces of the circular holes.

14. The system of claim 1, wherein internal stresses carried by the plurality of second components when the digits are closed around the object are greater than an ultimate tensile stress of the first material.

15. The system of claim 1, wherein:
    the plurality of first components comprise a 3D thumb shape with exterior surfaces resembling a thumb of the human hand; and
    the plurality of second components comprise a set of additional flat shapes that are engageable with the 3D thumb shape to define an operational linkage operable to close the thumb responsive to the pull force.

16. The system of claim 15, wherein the set of additional flat shapes comprise a thumb link that is fixedly engageable with the 3D thumb shape and operable to transfer the pull force from the operational linkage to the 3D thumb shape.

17. The system of claim 1, wherein:
    the additional force transfer elements comprise:
        a ratchet engaged with a first one of the upper arm prosthetic and the lower arm prosthetic; and
        a pawl engaged with a second one of the lower arm prosthetic and the upper arm prosthetic,
    and lifting the lower arm prosthetic interacts the ratchet with the pawl to prevent the lower arm prosthetic portion from lowering.

18. The system of claim 17, wherein the additional 3D shapes comprise an elbow body and the system further comprises an elbow spring that is engaged with the elbow body and the pawl so that:
    expanding the spring disengages the pawl from a first tooth of the ratchet; and contracting the spring engages the pawl with a second tooth of the racket.

19. The system of claim 17, wherein the rachet is engageable with the pawl so that upper arm prosthetic is not rotatable relative to the lower arm prosthetic.

20. The system of claim 19, wherein the additional force transfer elements comprise a release operable to disengage the ratchet and the paw so that upper arm prosthetic rotatable relative to the lower arm prosthetic.

21. The system of claim 20, wherein the plurality of first components are 3D printed from the first material and the plurality of second components are cut from a single sheet of the second material using a laser cutter or a water jet cutter.

22. The system of claim 1, wherein:
the first flat plates comprise a plurality of finger couplers;
the at least one second flat plate comprises a slide plate with holes; and
the plurality of finger couplers pass through the holes when opening and closing the digits.

23. The system of claim 22, comprising a spring that is:
captured between a side of the slide plate and an end of one finger coupler of the plurality of finger couplers; and
operable to bias the end of the one finger coupler away from the slide plate.

\* \* \* \* \*